United States Patent
Shachar

(10) Patent No.: US 7,588,564 B2
(45) Date of Patent: Sep. 15, 2009

(54) APPARATUS FOR PIEZOELECTRIC LAYER-WISE PUMP AND VALVE FOR USE IN LOCAL ADMINISTRATION OF BIOLOGICAL RESPONSE MODIFIERS AND THERAPEUTIC AGENTS

(75) Inventor: Yehoshua Shachar, Santa Monica, CA (US)

(73) Assignee: Pharmaco Kinesis Corporation, Inglewood, CA (US)

(*) Notice: Subject to any disclaimer, the term of this patent is extended or adjusted under 35 U.S.C. 154(b) by 388 days.

(21) Appl. No.: 10/614,685

(22) Filed: Jul. 3, 2003

(65) Prior Publication Data
US 2004/0078027 A1 Apr. 22, 2004

Related U.S. Application Data

(60) Provisional application No. 60/393,933, filed on Jul. 3, 2002.

(51) Int. Cl.
*A61K 9/22* (2006.01)
*A61M 31/00* (2006.01)
*F04B 17/00* (2006.01)

(52) U.S. Cl. .............. 604/891.1; 604/65; 417/413.2
(58) Field of Classification Search .............. 604/890.1, 604/891.1, 65–67; 417/413.2, 322
See application file for complete search history.

(56) References Cited

U.S. PATENT DOCUMENTS

| | | | | |
|---|---|---|---|---|
| 5,569,187 A * | 10/1996 | Kaiser | ......................... | 604/67 |
| 6,206,914 B1 * | 3/2001 | Soykan et al. | ............... | 623/1.42 |
| 6,379,323 B1 * | 4/2002 | Patterson | ........................ | 604/8 |
| 6,479,052 B1 * | 11/2002 | Marshall et al. | ............. | 424/93.7 |
| 6,541,021 B1 * | 4/2003 | Johnson et al. | .............. | 424/422 |
| 6,589,229 B1 * | 7/2003 | Connelly et al. | ......... | 604/890.1 |
| 6,749,587 B2 * | 6/2004 | Flaherty | ..................... | 604/151 |
| 2002/0090388 A1 * | 7/2002 | Humes et al. | ................ | 424/422 |
| 2003/0069541 A1 * | 4/2003 | Gillis et al. | ............ | 604/164.01 |

\* cited by examiner

*Primary Examiner*—Kevin C Sirmons
*Assistant Examiner*—Andrew M Gilbert
(74) *Attorney, Agent, or Firm*—Daniel L. Dawes; Marcus C. Dawes

(57) ABSTRACT

A method and apparatus for local infusion of a variety of biological response modifiers (BRMs) and chemotherapeutic agents including tumor necrosis factors (TNF) is described. In one embodiment, the device contains a synthetic pouch compartmentalized into three or more chambers, and an electronic apparatus controlling and modulating the delivery of the agents to the site of the tumor, so as to achieve a desired regimen in support of the elimination of a tumor burden. In one embodiment, an electronic system provides tailored and controlled regulation of the administration of such agents, using sensors to monitor the progress of the treatment. Desired dosing and scheduling of anti-tumor agents in a local setting is provided. In one embodiment, active control and regulation of the administration of medicating agents is attached to a synthetic pouch and with the aid of a piezoelectric valve and pump actuating mechanism. The apparatus provides the desired dose, duration and timing of dose delivery. In one embodiment, reporting the events in the tumor site via an RF link to the external control box is provided.

56 Claims, 15 Drawing Sheets

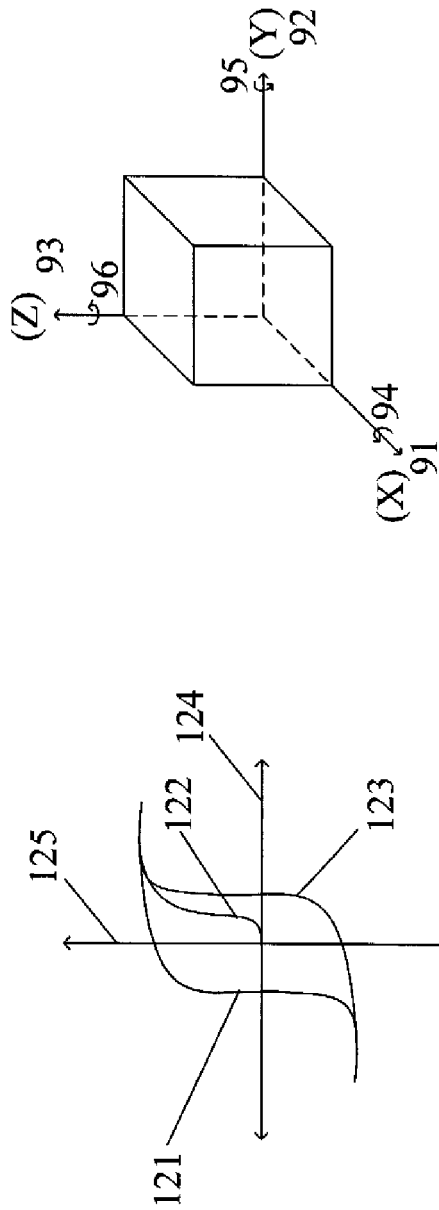
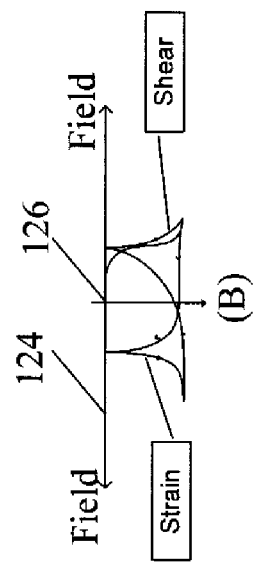
FIG. 6a
FIG. 6b
FIG. 6

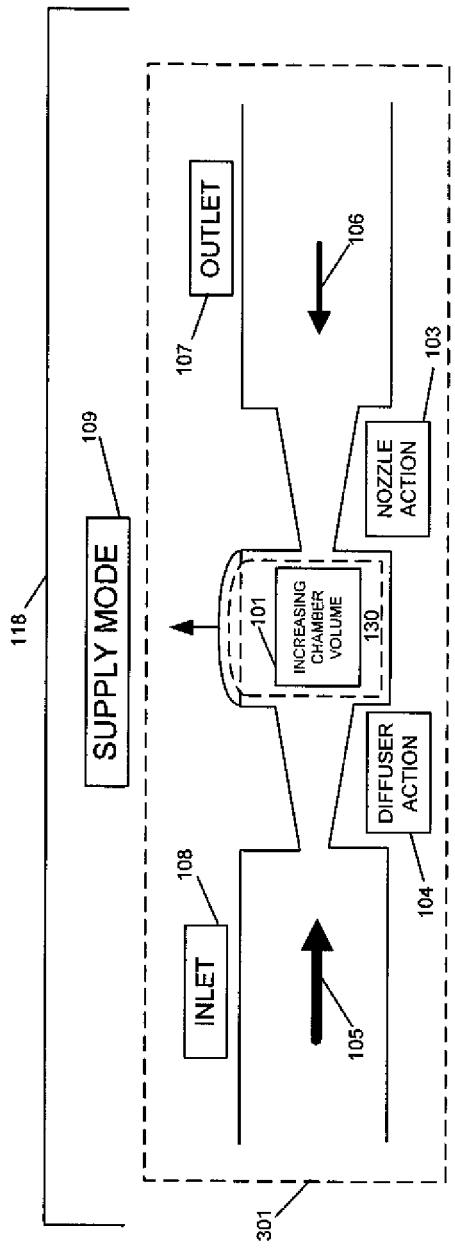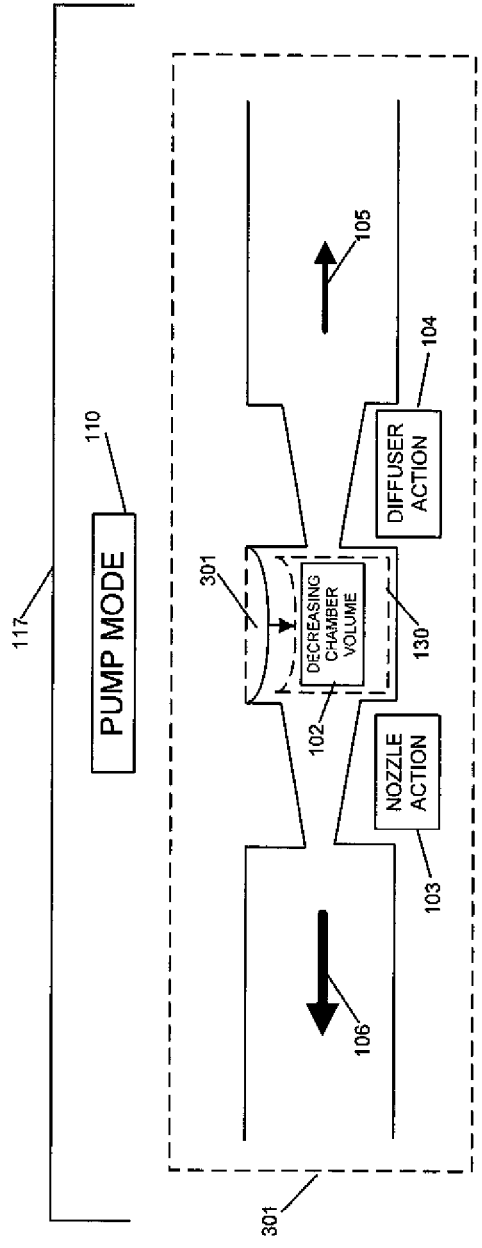

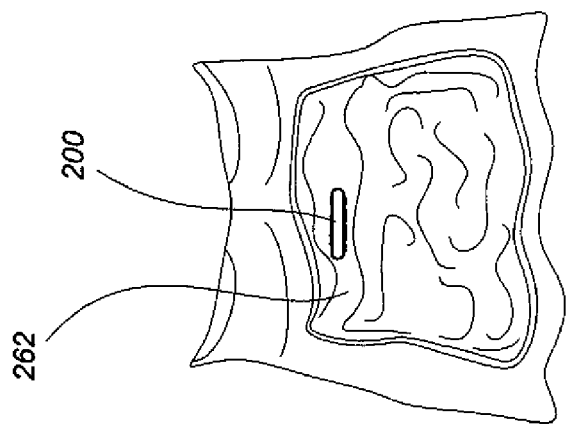
FIG. 8c
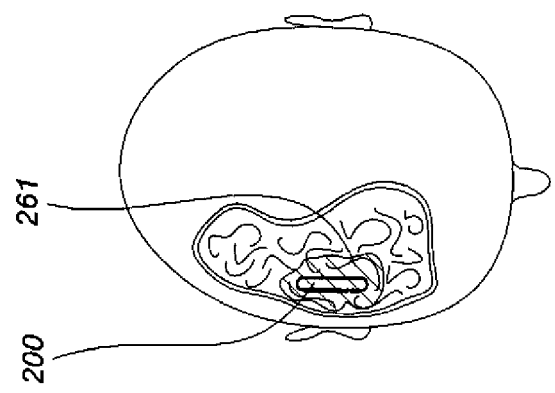
FIG. 8b
FIG. 8
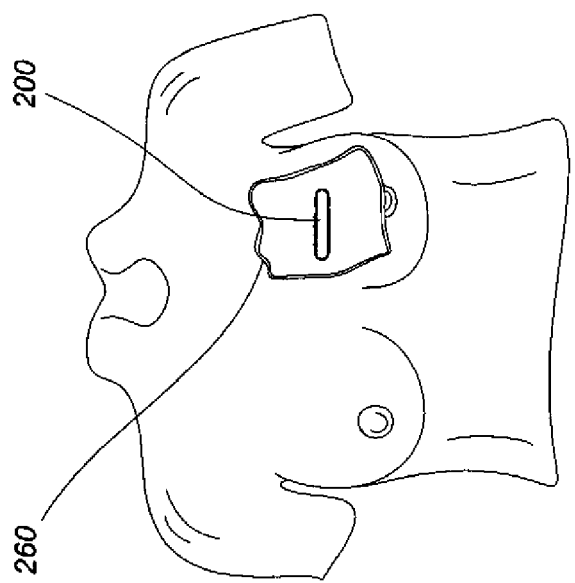
FIG. 8a

APPARATUS FOR PIEZOELECTRIC LAYER-WISE PUMP AND VALVE FOR USE IN LOCAL ADMINISTRATION OF BIOLOGICAL RESPONSE MODIFIERS AND THERAPEUTIC AGENTS

REFERENCE TO RELATED APPLICATIONS

The present application claims priority benefit of U.S. Provisional Application No. 60/393,933, filed Jul. 3, 2002, titled "METHOD AND APPARATUS FOR PIEZOELECTRIC LAYER-WISE PUMP AND VALVE FOR USE IN LOCAL ADMINISTRATION OF BIOLOGICAL RESPONSE MODIFIERS AND THERAPEUTIC AGENTS", the entire contents of which is hereby incorporated by reference.

BACKGROUND

1. Field of the Invention

The present invention relates generally to implantable medical devices, and more particularly to an improved operating system architecture incorporating a piezoelectric layer-wise pump and valve for use in local administration of biological response modifiers and chemotherapeutic agents in tumor fighting.

2. Description of the Related Art

The underlying hypothesis of using cytotoxic drug is that more is better. Thus, a first step in administrating a cytotoxic agent is to determine the maximum tolerated dose (MTD). However, when used in traditional treatment modes, such as chemotherapy, the cytotoxic agents are delivered to the patient in a manner that allows the cytotoxic agents to be distributed more or less globally throughout the body of the patient. Relatively large doses of the drugs are required since only a small fraction of the administered dose will be present at the tumor site at any given time. The remainder of the dose will be in other parts of the body. Moreover, a major problem with conventional chemotherapy is the lack of specificity of the cancer cell.

The use of large doses of toxic agents often leads to serious and debilitating side effects. Moreover, the global administration of drugs is often not compatible with combination therapies where a number of medicating agents are used synergistically to treat tumors or other conditions. Thus, the global administration of medicating agents to treat tumors and other such medical conditions is an inefficient, often dangerous, technique that often leads to severe or debilitating side effects.

SUMMARY OF INVENTION

The present invention solves these and other problems by providing a system and method for dispensing medicating agents, controlling, regulating, and optionally reporting the results of such agents at the tumor site of a patient. One embodiment provides a system where monitoring and reporting of biological response parameters are maintained in the resident memory of the system. One embodiment includes an implantable piezoelectric layer-wise pump and valve for use in local administration of medicating agents. In one embodiment, an implantable apparatus is used to assist in improving the art of dispensing medication to tumors where effective use of the agents (BRMs Chemo, TNF, and others) is a definite dose and timeline to produce tumor burden elimination or reduction. In one embodiment, medicating agents include agents, such as biological response modifiers, enzymes, therapeutic agents, drugs, chemotherapy agents, and the like.

One embodiment is configured to enhance the mechanism of vectorial change of the tumor escape mechanism by introducing a sufficient tumor antigen to stimulate the immune system of the patient. One embodiment is configured to assist in irrigating the solid tumor by increasing the number of cell adhesion molecules which are used for the adherence of cytotoxic cells to target cells before lysis can ensue, (the malignant cells cannot bind to cytotoxic cells thereby escaping immune surveillance) and local administration of cytotoxic cells by the use of the apparatus will improve and enhance such a process.

One embodiment is configured to administrate biological response modifiers (BRMs) with an improved dose, local delivery and scheduling on a case specific basis using a programmable microcontroller and its associated valve mechanism.

One embodiment is configured to allow the clinician the ability to prescribe an optimal biological dose (OBD) as opposed to maximum tolerated dose (MTD) by the use of a control mode defined by its programmability and its logic, which is embedded in the microcontroller look-up-tables. One embodiment is configured to incorporate the pharmacokinetic and pharmacodynamic parameters associated with chemotherapeutic agents to achieve the desired results without the toxic side effects known to those familiar with the art.

One embodiment is configured to modulate and modify the output of the medicating agents during treatment by changing the procedure in real time through the use of a command structure of the microcontroller look-up-tables with the use of a communication link built into the apparatus. One embodiment is configured to regulate the rate of dispensation of the medicating agents by modifying the duty cycle of the valve located in the apparatus. One embodiment is configured to regulate the intake of the tumor BRMs due to their pleiotrophic nature, and allow for processes and mechanisms to develop by reducing or enhancing the various agents in the medicating pouch, hence providing a treatment specific to the patient (e.g. tumor size, lysis, etc.).

One embodiment is configured to control and regulation capabilities to provide actions specific within a time domain such as the introduction of interferon alpha to tumor site (INF-2), whose immune modulating effects and/or anti-proliferate effects and dosing can be very different depending on which effect is to be maximally stimulated. One embodiment is configured to provide maximum dosing of chemotherapeutic agents to the tumor site by using the maximum tolerated doses (MTD) on a time domain which does not interfere with the activity of BRMs through the use of the selective control of the valve actuating mechanism built in the apparatus.

One embodiment is configured to provide the clinician a way to allow the expression of BRMs cascade effects (due to the communication of cytokines as messengers with their synergistic, additive or antagonistic interactions that affect the target tumor cells). One embodiment is configured to provide scheduling of medicating agents such as chemotherapy and BRMs based on their toxicity, and to allow for measures such as bioavailability, solubility, concentration, and circulation based on locality, both of which are an improved approach to the elimination solid tumors.

One embodiment is configured to address the individual differences of various tumors based on the disease stage, immune factors, body weight, age and chronobiology through the ability of the apparatus to locally administer the agents, dosing and scheduling.

One embodiment is configured to mitigate the known factors such as peak serum concentration, (generally associated with peak occurrence of side effects on IFN intravenously injected, which serves as a typical model) whereby the peak concentration of IFN is correlated clinically with peak side effects.

One embodiment is configured to support clinical studies and to demonstrate that responses to BRMs such as IFN-gamma follow a bell shaped response curve whereby when the concentration of the drug increases so does its response, hence the availability of the apparatus with its local administration of drug delivery affords an improved use of such processes.

One embodiment is configured to provide an effective mode of administrating BRMs with chemotherapy as a combination therapy by making available a local administration of different IFNs with IL-2, or IL-2 in combination with monoclonal antibodies and tumor necrosis factors (TNFs), and scheduling by the use of the invention.

One embodiment is configured to enable drug manufacturers to evaluate the effectiveness of its drugs during animal and clinical studies by providing the details and feedback on the use, dose, cycle, circadian time effects and the entire pharmacokinetic and pharmacodynamic behavior of the medicating agents not as verbal reports of symptomology chronicles by the patient but as a biological measure of tumor responses to the agents.

One embodiment is configured to implant the apparatus in the neighborhood of the tumor site for effective local delivery of the medicating agents.

One embodiment is configured to provide a method and apparatus for local administration of BRMs and chemotherapeutic agents, to enhance mechanisms that support overlapping effects in reducing tumor burden and elimination of tumors. To induce an improved response by the use of biomodulators (augmenting the patient's anti-tumor response via production of cytokines), decreasing suppressor mechanisms, increasing the patient's immunological response, limiting the toxicity of such agents (by the locality), maximizing the dose, increasing susceptibility of cells membrane characteristics for improved chemotherapy results at the site, and decreasing the tumor's ability to metastasize.

The above characteristics are measurable elements as dosing and scheduling improves the effectiveness of chemotherapy on malignant cells and reduces the exposure of such toxins to normal tissues. One embodiment provides improved immunomodulation with relatively little immuno-suppression. One embodiment can be used by a variety of clinical techniques such as the Creech technique of regional or isolated limb perfusion to administer high-doses of chemotherapy to an isolated site of melanoma or sarcoma. This technique is used by BRMs and TNF-α have anti-tumor effects by damaging the neovascular circulation surrounding tumors without destroying normal tissue. The fact that the effective use of TNF-α cannot be administered systemically due to its toxic effects (septic shock) is just a model for the varieties of cytotoxic as well as chemotherapeutic agents, hence the use of local administration by the apparatus is beneficial. One embodiment provides for defining an improved dose and schedule of biological agents to maximize the anti-tumor effects of each agent while not increasing toxicity to the patient. Treatment modality by the use of combination therapy and local administration of such agents on a specific schedule is one of the benefits of the invention.

BRIEF DESCRIPTION OF THE DRAWINGS

The various features of the present invention and the manner of attaining them will be described in greater detail with reference to the following description, claims, and drawings, wherein reference numerals are used, where appropriate, to indicate a correspondence between the referenced items.

FIG. 1 is a high level block diagram of the implantable apparatus having a piezoelectric pump for local administration of medicating agents such as biological response modifiers, chemotherapeutic agents, etc., which is shown in dotted outline in FIG. 1a.

FIGS. 6, 6a, and 6b are graphs which illustrate how polarization of the "electrostatic muscle" produces shear and strain.

FIGS. 6c, 6d, are diagrams which depict the "electrostatic muscle" states, showing the closed or pump mode in FIG. (6c) and showing the open or supply mode in FIG. (6d).

FIG. 6j is a partially exploded view.

FIGS. 8a-8c shows three possible cases of the pouch as it is placed inside the body. The figures illustrate the apparatus implanted in tumor sites: in FIG. 8a, the apparatus is implanted to treat ductal carcinoma of the breast, (DCIS), in FIG. 8b the apparatus is implanted to treat meningioma in the periocular region of the head, and 8c, Transverse Colon tumor.

DESCRIPTION

Figure 1:
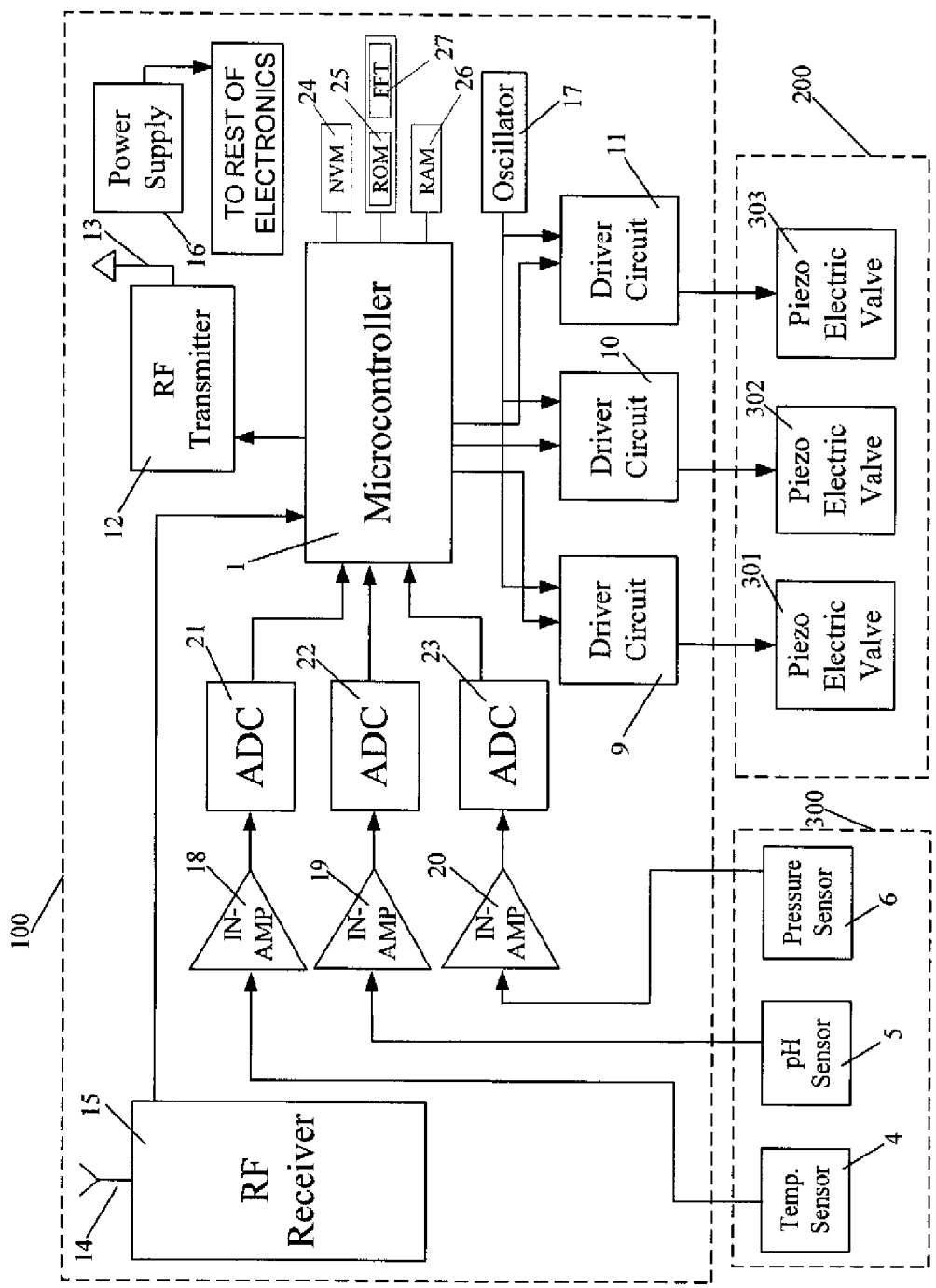

The system described herein relates to medical apparatus containing a valve, a pump, and a reservoir. The apparatus includes means for regulating, controlling, and modulating a combination therapy of cytokine and chemotherapeutic agents for the purpose of tumor elimination. Biotherapy and combination therapy, using medicating agents such as, for example, biological response modifiers (BRMs) as agents or approaches, modifies the relationship between tumor and host, hence modifying the host's biologic response to tumor cells and chemotherapeutic agents. This combination therapy method has shown improved therapeutic indices. Hence, treatment of tumor with the use of BRMs and chemotherapy is copasetic with the principal goal where the patient must first achieve a complete response.

The approach of using combination therapies with the intent of increasing response rate due to synergetic effects of BRMs, due to their redundant and pleiotrophic nature (combinations of cytokines with chemotherapy) provides improved treatment of the tumor. A variety of combinations of BRMs, (such as different Interferon INF (.alpha., .beta., .gamma.) and of Interleukins (IL-2) or tumor necrosis factor (TNF) with IFN or IL-2 are some of the varieties of combinations in question) improve the results of tumor elimination.

IL-2 appears to act primarily as an immunomodulator whereas IFN has anti-proliferate effects. The use of BRMs and chemotherapy in combination of biotherapy is based on the rationale that the interaction of cytokines and cytotoxic drugs may occur on several levels, different mechanisms of actions; attacking the tumor, by modulating the pharmacokinetics of the chemotherapeutic agents as key enzymes (irrigation of solid tumor), attenuation of drug resistance mechanisms, modifications in permeability of the vascular system which allow increased accumulation of chemotherapeutic drugs at the tumor site, and reduction of tumor burden. The use of one modality to improve anti-tumor response increases production of cytokines, decreasing suppressor mechanisms. Other modalities are the patient's tolerance to cytotoxic effects, changing membrane characteristics of tumor cells (making it more susceptible to killing by chemotherapeutic agents) and decreasing the ability of tumor cell to metastasize.

The biomodulation action of the present system is described as manipulating the metabolic pathway of a cytotoxic drug to increase the efficacy of selective protection of normal tissue. The target of modulations includes specific enzymes of drug metabolism, receptors for adhesion or growth, cell cycle phases, gene expression and immune system. In one embodiment, proper dosing and scheduling are used to obtain benefits in a combination of chemotherapy with biotherapy. The apparatus can be used for combination therapy such as IFN-α with 5-FU (5-fluorouracil) and chemotherapy paired with IL-2 and IFN-α in improving the effectiveness of tumor elimination.

The impact and efficacy of Tumor Treatment using BRMs and chemotherapy often requires that specific intricacies of physiologic and pharmacologic parameters be thoroughly measured. This complete evaluation measures not only the agent's effectiveness but also takes into account cellular immune response. The steps for identification, isolation, recombinant expression and the physiological role as defined by the therapeutic model, are set by defining the pharmacokinetic as well as pharmacodynamic of the combination therapy.

The underlying hypothesis of cytotoxic drug is that more is better. Thus a critical first step in administrating a cytotoxic agent is to determine the maximum tolerated dose (MTD). Clinical trials of BRM's demonstrated that immunologic effects occur at doses lower than the identified maximum tolerated dose (MTD). This phenomenon led to the concept of optimal biological dose (OBD). The hypothesis and the clinical facts lead to determine that OBD is that which, with a minimum of side effects, produces the improved desired response for the parameters deemed important with respect to a particular biological agent".

Biological response modifiers, unlike drugs, have preprogrammed mechanisms and receptors available for them, which account for the difference between maximum tolerated doses (MTD) and optimal biological dose (OBD). Whereas cytotoxic agents possess the ability to maximize direct anti-tumor effects, BRMs are both cytotoxic and pleiotrophic and have indirect immune cascades that mediate the tumor physiology and maximizes the tumor response.

The above hypothesis and clinical observations show the desirability of administration cycle of BRMs and chemotherapeutic agents on scale and measure which does not lend itself to the traditional approach of maximum tolerated dose. Hence, the ability to regulate and schedule the dose of the BRMs and/or chemotherapy is essential and is addressed by this system.

The disclosed system and method yields a better correlation between BRMs using cytokines such as Interferon (IFN), Interleukins (IL), Hematopoietic factors (HGF), Monoclonal antibodies (MAB), and Tumor Necrosis Factor (TNF) in combination therapy with chemotherapeutic agents in achieving the desired goal of complete response.

The approach disclosed, using biotherapy with chemotherapy as treatment modality for cancer is not viewed as independent factors, but instead as an element of complex, intricate network producing a distinct response in overlapping effects. BRMs possesses the phenomenon of pleiotrophic effects, a single stimulus can induce a response from multiple cytokines including stimulating production of other agents, modulating receptor sites, and enhancing or inhibiting the biological activity of other cytokines. No therapy on its own (such as Interferon .alpha., .beta., .gamma. TNF-.alpha., .beta., .gamma. angiogenetic drugs, anti-sense therapy, interleukins 1-12, hematopoietic growth factors, monoclonal antibodies and the variety of chemotherapeutic agents), has generated the "magic bullet" for curing cancer. A new rational approach which combines the known characteristics of tumor physiology and the cascades of biological response modifiers including BRMs optimal biological dose (OBD) as well as chemotherapeutic maximum tolerated dose (MTD) is used as clinical observation indicators.

Since BRMs cascade effects are somewhat known to those familiar with the art, and chemotherapeutic effects of cell deaths are a preprogrammed events, the use of the apparatus and its associated circuitry will enhance and/or modulate a variety of tumor growth factors and will enable a combination therapy to take place on the tumor site without the known side effects due to maximum dose of toxins. The ability of the apparatus to change its preprogrammed sequence of events such as the release of various agents on a specific schedule and dose is due to the innate capability of the apparatus to receive commands via its communication links. This allows a treatment change in mid-stream by transmitting program codes, which instruct the microcontroller to enhance one process or another. The ability of the apparatus to modulate and enhance tumor cells' death is the mainstay of the technology disclosed.

The chemo immunotherapy model, by the use of the disclosed apparatus, allows the clinician to perform a selective treatment by preprogramming the targeted results. A typical example cited by clinical observation is Interferon α and 5-fluorouracil and calcium liucovorin combination of dacarbazine, BCNU, cisplatin, and tonoxifen, followed by interferon α and IL-2.

The above are examples of some of the approaches that can be used by a clinician in treating a tumor. In one embodiment, a multi-chamber pouch-type architecture with a preprogrammed instruction set allows the timed release of the agents discussed above. An "electrostatic muscle" enables the clinician to interfere and reduce or increase/change the medicating agent release based on tumor specific behavior (using known techniques of verification such as fluoroscopic and thermographic imagery to measure the success of the procedure by indicating reduction of tumor burden and tumor size) is the mainstay of the system and its embodiments.

In one embodiment, the apparatus can monitor and report to the clinician a set of biometric measures such as the temperature and the pH level at the tumor site, as well as the pressure of the tumor surrounding tissue. These are biometric measures and indications of the behavior of the tumor and its treatment history, and give the clinician an added insight on the progress of the treatment and the response of the tumor to the treatment. This is due to the pronounced changes of these biometric indications in the vicinity of the tumor as a result of its biological activity, its response to medication, and its on-going growth or decay. For example, in the case of pH measurement, it is known that the extracellular pH of solid tumors is acidic. This acidic pH can have many consequences which are germane to the etiopathogenesis of cancer. Low pH causes tumorigenic transformation of primary Syrian hamster embryo cells. It is also known that low pH causes chromosomal rearrangements in Chinese hamster embryo cells. Low pH also induces immediate early gene expression and activates the proto-oncogene RAS, in kidney renal tubule. Low Ph also increases in vitro migration and invasion. Culturing cells in a low pH environment causes them to be more metastic in vivo. Low pH also induces the expression of platelet-derived endothelial cell growth in tumors in vivo. It is also known that low pH enhances resistance to weakly basic chemotherapeutic drugs.

Tumor cells generally metabolize lipids and glucose different from their normal counterparts and these have significant sequelae that are germane to the transformed phenotype. For example, tumors maintain elevated levels of phosphomonoesters, which are precursors to the metabolism of phospholipids. These are related to the tumorigenicity and proliferation in a complex way and are markers for therapeutic effectiveness. Low extracellular pH can also promote a more aggressive tumor phenotype. A low interstitial pH is exacerbated by the fact that the tumor vasculature is inefficient. This inefficient vasculature also causes significant hypoxia, which contributes to the resistance of tumors to radiotherapy. The intercellular pH of cells in tumors is neutral-to-alkaline, which is used for continued cell proliferation.

Additional biometric measurements are available from pressure and temperature sensors embedded inside the apparatus. A major problem with conventional cancer therapy, such as radiotherapy and chemotherapy, is the lack of specificity of the cancer cell, except in the case of tumor tissue where high interstitial fluid pressure and elevated temperatures are shown to exist in tumor tissue as compared with those of a normal tissue. A step pressure gradient typically exists at the periphery of the tumor. Information relating to pressure gradient and temperature between the tumor site and the apparatus can assist the clinician in evaluating the treatment history and its progress. For example, it is known that chemical and blood vessel activity in both pre-cancerous tissue and the area surrounding a developing breast cancer is almost always higher than in normal breast tissue. In an ever-increasing need for nutrients, cancerous tumors increase circulation to their cells by opening existing blood vessels and creating new ones (neoangiogenesis). This process frequently results in an increase in regional surface temperatures of the breast. These temperature variations may be among the earliest signs of breast cancer and/or a pre-cancerous state of the breast. Hence the incorporation of a temperature sensor to allow the monitoring of temperature variations in correlation with treatment history provides the clinician with a set of valuable information relating to the progress in treating the tumor.

Cancerous cells generate more heat than healthy cells, due to hypervascularity or greater blood flow to the area, so tumors tend to be "hotter" when viewed using methods such as thermotherapy. Breast thermograms are related to growth rate of breast carcinoma, and thermography can be used as a preliminary screening procedure.

Angiogenesis pertains to the development of blood vessels or blood supply and plays a role in the validity of thermotherapy. A tumor cannot grow bigger than a pinhead unless it establishes an independent blood supply. Certain types of vascular formations often precede the appearance of breast tumors on mammography, sometimes by more than a decade, but seem to go undetected or are considered normal asymmetry. When cancer is present, blood flow increases to the afflicted area and thus thermotherapy allows the clinician to find potential problem areas years before they become irreversible. In one embodiment, the apparatus described herein uses the fact that a tumor is generally hotter than its surroundings, a fact that makes the use of the disclosed device able to detect the tumor and chart the progress in its destruction. That is, as the tumor is destroyed its temperature is gradually reduced, until it reaches the temperature of the surroundings. It is the goal of the disclosed apparatus to eliminate the tumor and to be able to continuously monitor the progress in its treatment.

The system disclosed enables the clinician to administer the BRMs and chemotherapeutic agents on schedule as well as duration and sequence preprogrammed to meet clinical observations with the intended goal of meeting complete response.

FIG. 1 shows an architectural general block diagram of the complete implantable system, with a temperature sensor, 4, pH sensor, 5, pressure sensor, 6, and a microcontroller, 1, embedded in the apparatus to ultimately oscillate the piezoelectric resonators, 301, 302, 303, thereby dispensing the medicating agents. The power source, 16, supplies the power for the rest of the electronics to operate. A body temperature sensor, 4, measures the temperature of the tumor site, an essential element for hypothermia treatment needed in conjunction with certain clinical procedures. A pH sensor, 5, is used to detect the level of the pH value in the tumor area, an important measure of the acidity of the immediate surroundings of the tumor cells. A pressure sensor, 6, is also employed to measure the pressure differential between the host-body/tumor-area and the pouch, 200. Sensors 4, 5, and 6, are linked via three instrumentation amplifiers, 18, 19, and 20, respectively, the purpose of which is to amplify the signals from sensors 4, 5, and 6. The outputs of the amplifiers 18, 19, and 20, connect to three analog-to-digital converters, ADCs 21, 22, and 23, respectively, the purpose of which is to convert the analog signals from the sensors to its equivalent digital representation. The outputs of the ADCs, 21, 22, and 23, connect to the microcontroller 1. In addition, three piezoelectric resonators driver circuits, 9, 10, 11, and oscillator, 17, are linked to produce the oscillating voltage which is used for the piezoelectric valves, 301, 302, 303, respectively, to operate. The above scheme is accomplished upon a command from the microcontroller, 1, which in turn receives its command either from its internal instructions sets, residing in non-volatile memory, NVM, 24, in ROM, 25, and/or in RAM, 26, or from an external source via the RF Receiver, 15, and its antenna 14. The microcontroller, 1, is also connected to RF transmitter, 12, which through its antenna, 13 sends the information collected by the microcontroller, 1 to an external data collection and retrieval station, 500 shown in FIG. 1a. The microcontroller 1 includes an optional module 27, a Fast Fourier Transform algorithm, which provides a scheme for digitally filtering identifying parameters that are used for the treatment of tumors using the pouch 200.

Figure 1A:
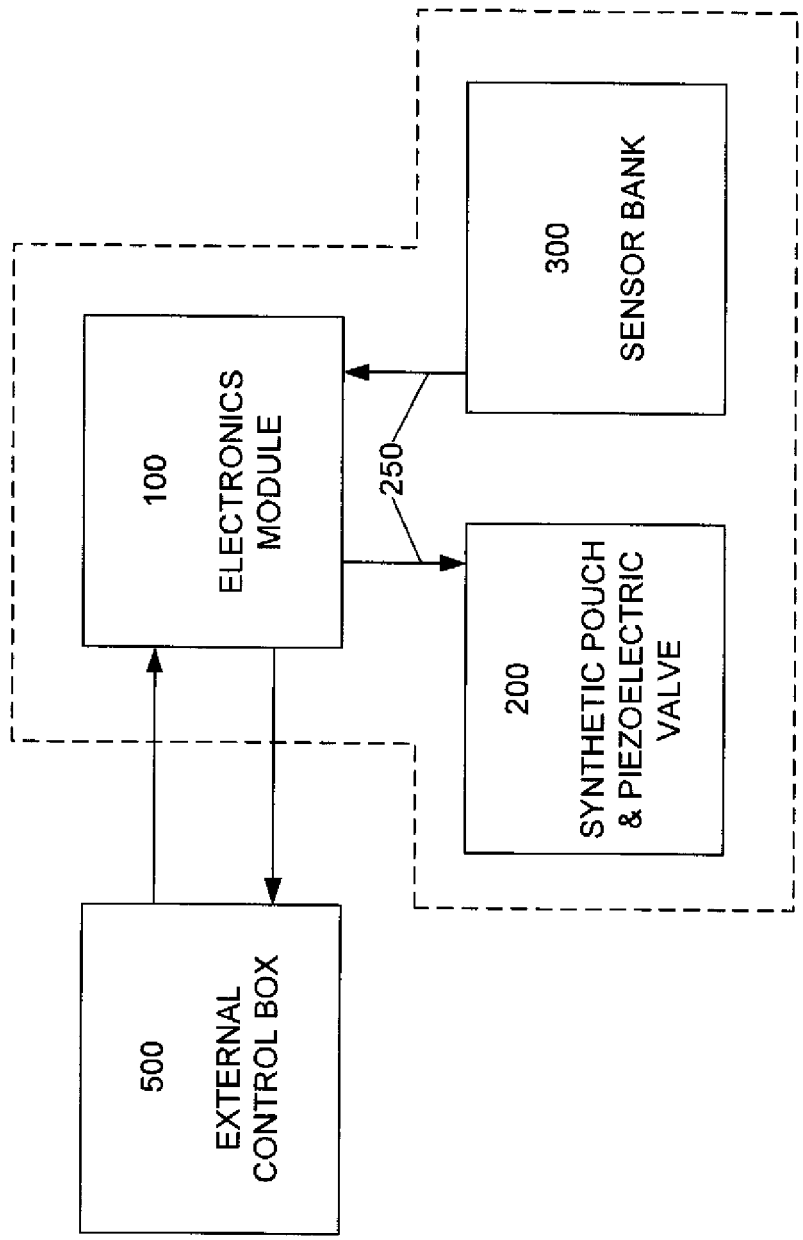
FIG. 1a is a system block diagram.

FIG. 1A is a high level system block diagram describing the relationship between the electronic module 100 and the synthetic pouch and its associated piezoelectric pumps/valves 200, including the sensor bank 300. It further depicts the hierarchy between the various modules of the system, such as the external control box 500 and its bidirectional communication link to the apparatus. A detailed description of the apparatus is further illustrated in FIG. 2. The architecture in the figure allows the system to be used in a modular fashion. For example, in one of the possible options pouch 200 with its associated valves, 301, 302, and 303, can be used where the electronic module 100 is inserted under the dermis and located remotely from the pouch 200, and connected to the pouch 200 via ribbon cable 250 indicated in FIG. 1a. This architecture provides the clinician with the option of inserting the pouch 200 into an area inside the human body where the apparatus is capable of operating for relatively long durations and thus allows the replacement of the battery with relative ease, as the electronic module 100 and its power supply including the battery are not necessarily co-located. This architecture further provides for the sensor bank 300 to be independently located in the vicinity of the pouch 200 but not necessarily on the pouch itself. Thus the sensor bank 300 and the electronic module 100 are interconnected via ribbon cable 250.

Figure 2:
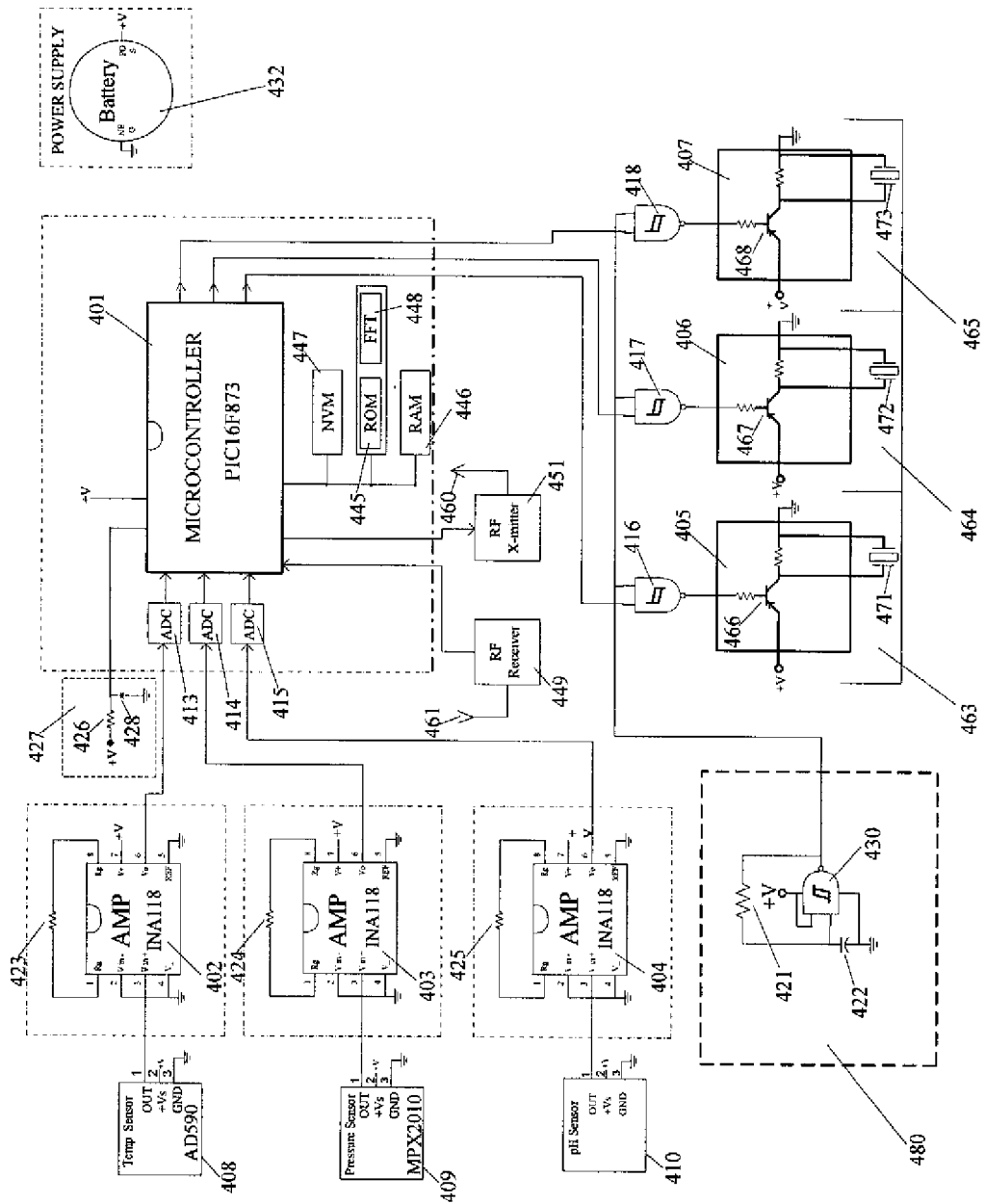
FIG. 2 is a schematic diagram of FIG. 1 depicting component part numbers and possible connections between the various elements.

FIG. 2 is a schematic diagram of the apparatus, as defined in the high level architecture noted in FIG. 1. A microcontroller, 401, such as the Microchip PIC 16F873, is used to control the various tasks of the apparatus. The microcontroller, 401, has three analog-to-digital inputs, 413, 414, and 415, respectively, which convert the analog signals from the sensors 408, 409, and 410, respectively, to their digital representation. Temperature sensor, 408, such as the Analog Devices part number AD590, feeds its signal to Instrumentation Amplifier, 402, such as the Burr-Brown part number INA118, the function of which is to amplify the signal from the temperature sensor 408, to a comfortable level that the microcontroller 401, can operate on. The gain of the amplifier 402 is determined by the value of the resistor 423, which is in the feedback loop of amplifier 402. Amplifier 402 then feeds its analog signal to ADC 413, which translates the signal from amplifier 402 to its digital representation. Pressure sensor, 409, such as the Motorola part number MPX2010, is used to monitor the pressure differential between the pouch and the tumor. The pressure sensor, 409, feeds its analog signal to instrumentation amplifier, 403, such as the Burr-Brown part number INA118, the function of which is to amplify the signal from the pressure sensor 409, to a comfortable level that the microcontroller 401, can operate on. The gain of the amplifier 403 is determined by the value of the resistor 424, which is in the feedback loop of amplifier 403. Amplifier 403 then feeds its analog signal to ADC 414, which translates the signal from amplifier 403 to its digital representation. Also utilized in this scheme is a pH sensor, 410, such as a solid-state ISFET device, whose function is to determine the acidity and/or basicity of the tumor's surrounding area. The pH sensor, 410, feeds its analog signal to Instrumentation amplifier, 404, such as the Burr-Brown part number INA118, the function of which is to amplify the signal from the pH sensor 410, to a comfortable level that the microcontroller 401, can operate on. The gain of the amplifier 404 is determined by the value of the resistor 425, which is in the feedback loop of amplifier 404. Amplifier 404 then feeds its analog signal to ADC 415, which translates the signal from amplifier 404 to its digital representation. The microcontroller 401 is run by its own external oscillator, 427, which is a resistor-capacitor network, made up of resistor 426 and capacitor 428, or it can use its own internal resistor/capacitor network for this purpose. The microcontroller, 401, comprises the Microchip PIC16F873, contains its own NVM, 447, ROM, 445, and RAM, 446, which can be in the form of Flash memory. The instruction set for the various operations of the apparatus are stored in the NVM, 447, ROM, 445, and RAM, 446. Upon execution of a command by the microcontroller 401, the results of the measurements from sensors 408, 409, and 410, are then processed and fed to RF transmitter 451, such as the Micrel part number MICRF102, and its antenna 460. The RE transmitter 451, with its antenna 450, sends the data to an external receiver where the operator/user can then analyze the data and change or modify the dosage and the delivery conditions. The modification of dosage and the delivery conditions by the user are fed back to the microcontroller 401, through RF receiver 449, such as the Micrel part number MICRF007, and its antenna 461. The output of the RE receiver 449 is fed to one of the digital inputs of the microcontroller 401, whereby the microcontroller 401 can continuously monitor the output of the RE receiver 449 and act upon the instructions that it receives from the clinician. The instruction set from the clinician is related to dosage and other parameters and conditions such as pH, temperature and pressure exerted by the tumor. The medicating agents are fed to the tumor from the three pouch compartments, by valve actuating mechanisms 463, 464, and 465, via the piezoelectric valves, 471, 472, and 473, respectively. Upon the application of a signal to the piezoelectric resonators 471, 472, and 473, the resonators oscillate and open a passage for the medicating agents as to allow flow from the pouch compartments valve actuating mechanisms 463, 464, and 465, respectively, to the tumor site, based on instruction set defined by the clinician for the specific treatment of the tumor. The piezoelectric resonators 471, 472, and 473, are activated upon a signal from the microcontroller 401, via NAND gates such as the Motorola MC14093, designated by 416, 417, and 418, respectively. The NAND gates 416, 417, and 418, have two inputs, where one input is fed from the microcontroller 401, and the other is fed collectively to three NAND gates from piezoelectric oscillator 480. Piezoelectric oscillator 480 is made up of a single NAND gate such as the Motorola MC14093 and it is of a Schmitt trigger type. Thus the piezoelectric oscillator 480 is made up of a Schmitt trigger NAND gate 430, a resistor 421, and a capacitor 422. The frequency of oscillation is low and it is determined by the values of the resistor 421, and the capacitor 422. The output of the oscillator 480 is a square wave type and it is fed to other three NAND gates, 416, 417, and 418. This signal operates the piezoelectric resonators, 471, 472, and 473, as these resonators use a signal in the form of a square wave. The resonators 471, 472, and 473, are driven by their own drivers, in the form of PNP transistors 466, 467, and 468, such as the National Semiconductor 2N3906. The NAND gates 416, 417, and 418 have their outputs true when their inputs, both from the microcontroller 401, and the piezoelectric element oscillator 480, are true. However the inputs are true high, and the outputs are true low, thus PNP transistors 466, 467, and 468 are used, as these are triggered by a low signal at their bases from the corresponding NAND gates. Transistors 466, 467, and 468 drive the piezo electric elements 471, 472, and 473, respectively, with a square wave signal from oscillator 480, upon a command from microcontroller 401. Such a command from microcontroller 401 is fed to NAND gates 416, 417, and 418, respectively, thus these NAND gates function as a one-way switch for the drive signal from oscillator 480. A power supply, 432, is in the form of a 6-Volt long-lasting alkaline battery such as the Duracell 7K67 or equivalent, and it supplies power for various electronics components inside the pouch.

Figure 3:
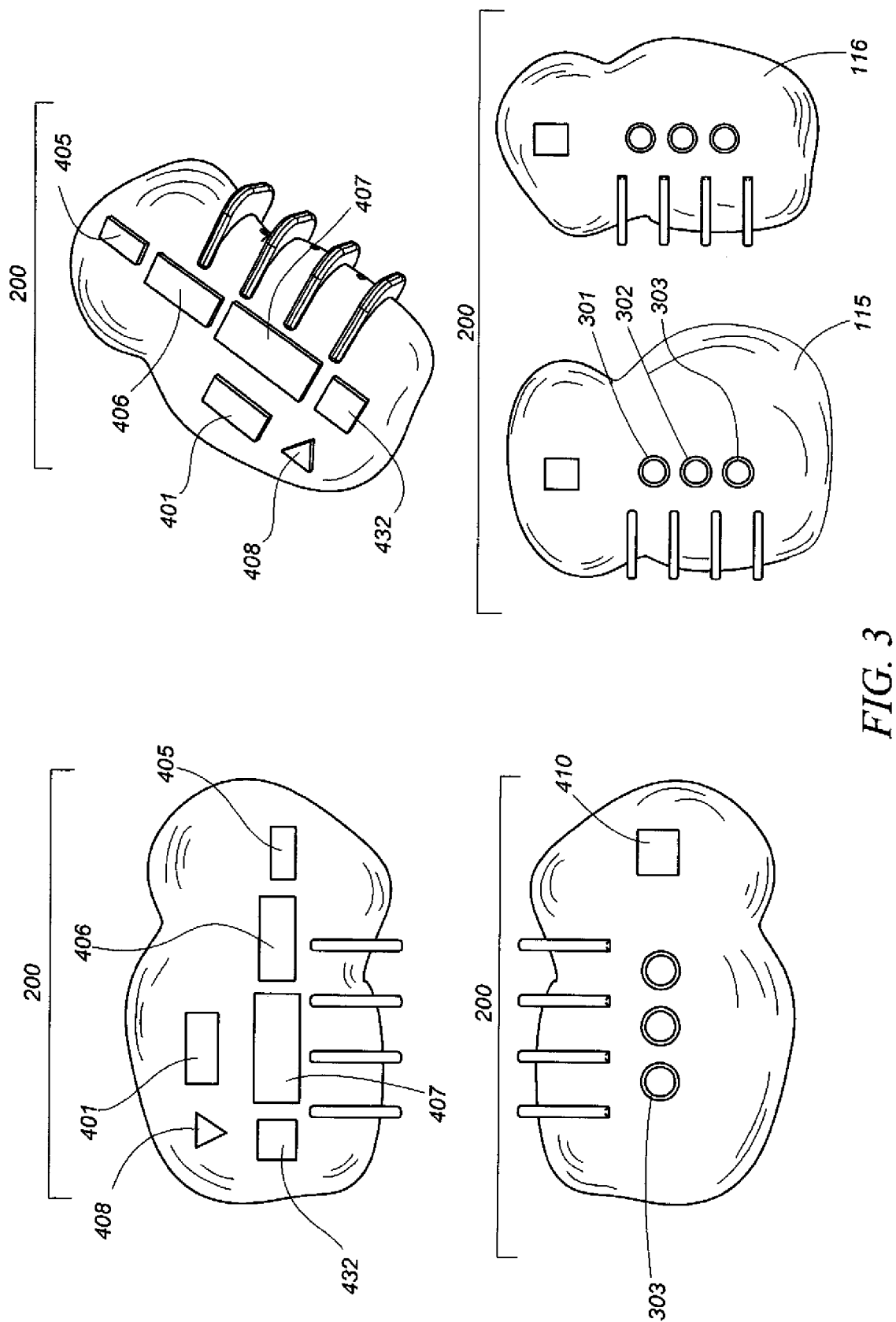
FIGS. 3a-3d are a plurality of perspective views of the implantable apparatus depicting different views of the medicating pouch and its associated valve mechanisms.

FIGS. 3a-3d are graphic perspective diagrams of the apparatus depicting different views of the medicating pouch and its associated valve mechanisms. In FIG. 3a the pouch 200 is depicted in its top plan view, showing the somewhat irregular shape of the pouch which is pliable and biodegradable. Additionally pouch 200 is shown in perspective view in FIG. 3b depicting a construction of the medicating container made of synthetic skin such as Integra shown in FIG. 6j as item 143, namely a skeleton of a porous matrix of fibers of cross-linked bovine tendon collagen and a chondroitin-6-sulfat with a skin layer made of synthetic polysiloxane polymer (silicone) known as Integra and is biodegradable. Pouch 200 contains three compartments for three different medicating agents 201, 202, and 203, corresponding to compartments a, b, and c, (not shown) respectively. The top view of FIG. 3a also shows the associated three piezo-electric valve assemblies, 405, 406 and 407. Also shown in the top view are the microcontroller 401, the temperature sensor 408, and the power source 432. The bottom plan view of FIG. 3c shows the pH sensor 410 and the three valve openings 301, 302 and 303. Through these valve openings the medicating agents flow out and medicate the tumor site. FIG. 3d further shows the two valve states, the open mode, 115, and the closed mode, 116.

Figure 4:
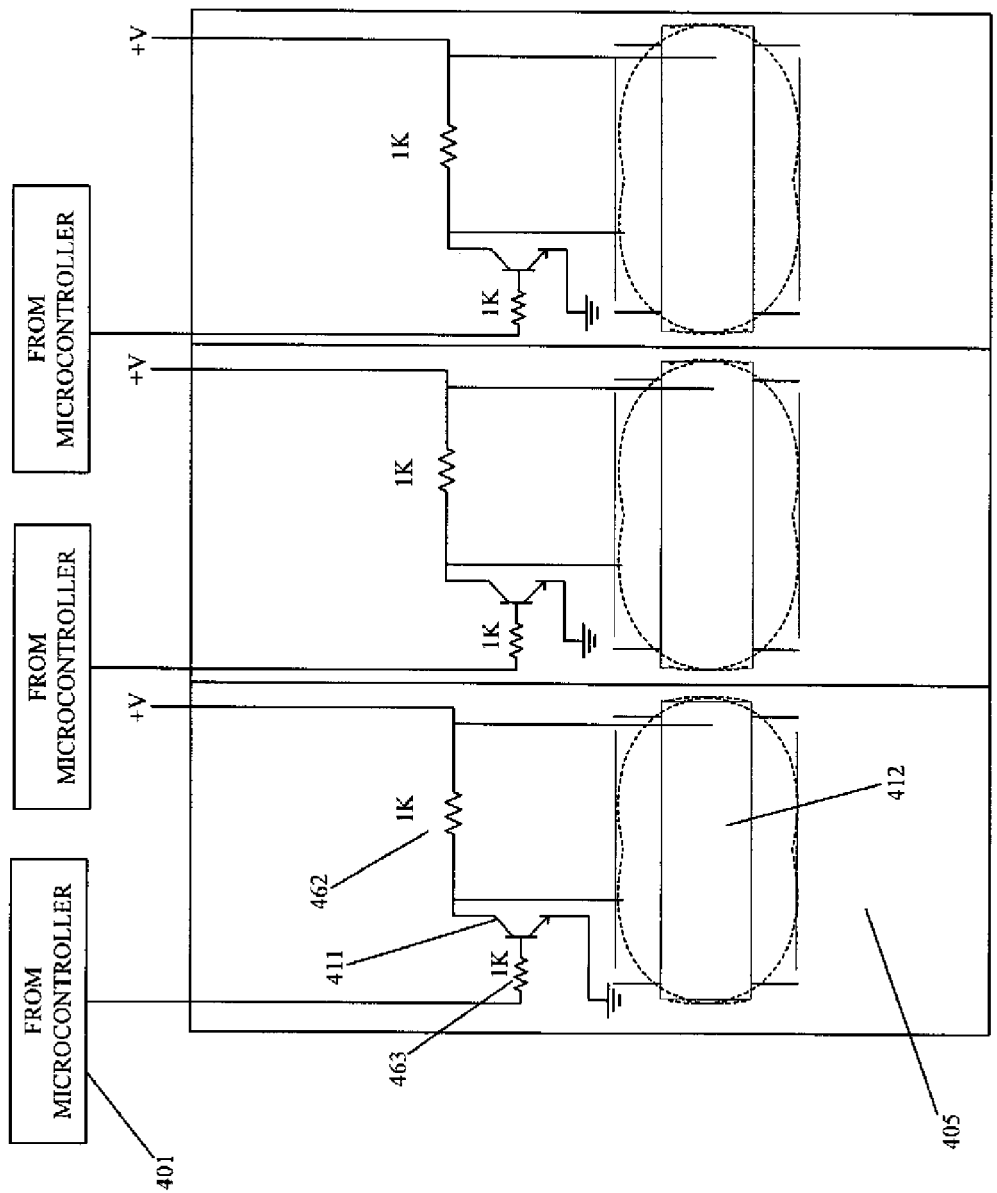
FIG. 4 is a detailed schematic of the external driver circuits which drive the piezoelectric resonators, which are the "electrostatic muscles."

FIG. 4 shows the three drivers for the three piezo electric valves. In the figure the drivers are made of an NPN transistor, 411, such as the National Semiconductor 2N3906, whose input is derived from the microcontroller 401. The signal from the microcontroller 401 is fed to the NPN transistor 411 through a base resistor 463. An additional resistor 462 is placed in the collector of the transistor 411. The piezoelectric valve 412 is placed in parallel to the collector resistor 462.

Upon a command from microcontroller 401, transistor 411 is turned on and off by the signal it receives from microcontroller 401. Its signal is amplified and is introduced to piezoelectric device 412, which in turn oscillate at the rate of the signal that it receives from transistor 411. This oscillation of the piezoelectric device 412 allows the medication to be dispensed through to the tumor site. The signal from microcontroller 401 is in the form of a square wave, and thus there is no need for an additional oscillator, as the signal can be obtained directly from the microcontroller 401. Alternately the square wave signal can be obtained from a dedicated oscillator 480, thereby relieving the microprocessor for other important tasks. Resistor 463 is a base current limiter and resistor 462 is the collector resistor for transistor 411, which allows for fast discharge of charge build-up across the piezo-electric device 412. The three compartments of the pouch are shown as drives 405, 406, 407 and respectively represent valve actuating mechanisms 463, 464, and 465 in FIG. 2.

Figure 5:
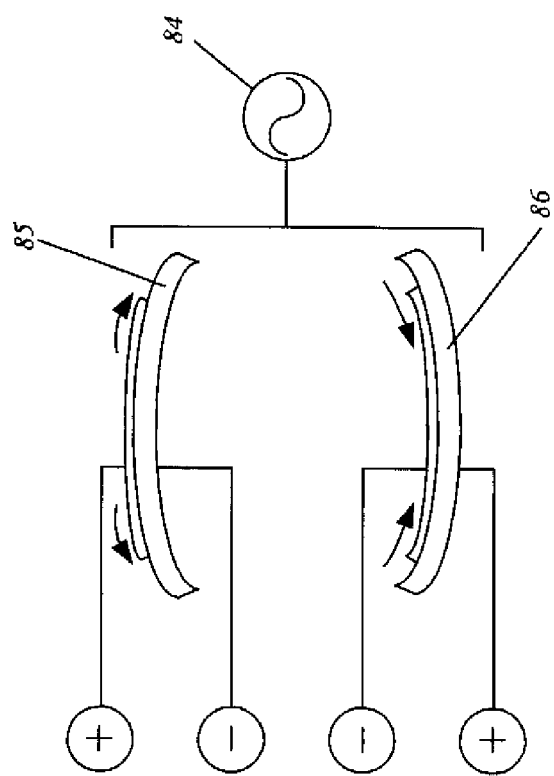
FIGS. 5a-5c are a plurality of views of the piezoelectric diaphragm with its physical structure, showing the piezoelectric diaphragm bending mechanism when the applied field is polarized. A top plan view and a side plan view of a single diaphragm is shown in the left side of the figure. A diagrammatic side plan view pair of activated opposing diaphragms is shown in the right side of the figure.
Figure 5:
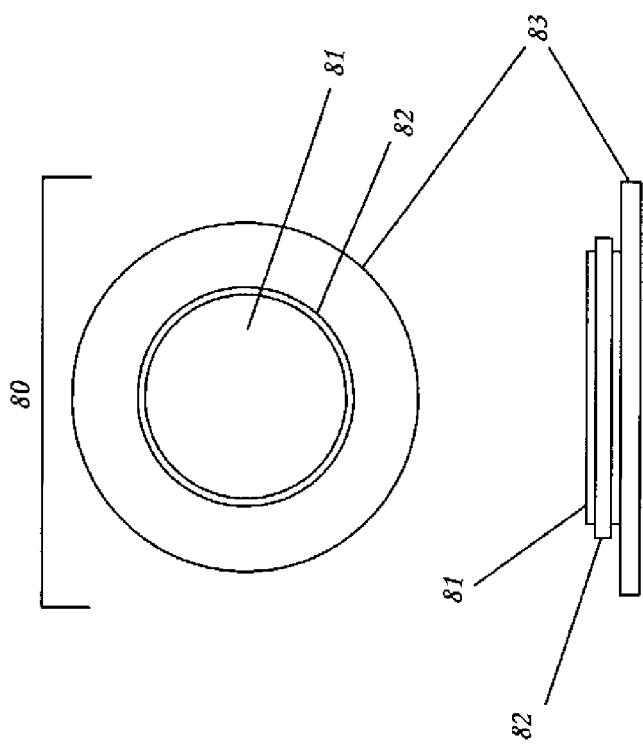

FIGS. 5a and 5b show a top plan view and side elevational view respectively of the piezoelectric diaphragm 80 with its physical structure, and show the piezoelectric diaphragm bending states 85 and 86 in FIG. 5c when the applied field is polarized. FIGS. 5a and 5b shows the piezoelectric ceramics 82 sandwiched between the electrode 81 and the metal plate 83. FIG. 5c also shows an extended state of the piezoelectric element 85 upon the application of an external signal, and a compressed state, 86, upon the application of a signal opposing to the original one shown in the extended state 86. The external signal 84 is applied to the ceramics from the microcontroller 401. When the oscillating signal 84 is applied across the electrodes 81, 82, and 83, the bending shown in 85 and 86 is repeated by the control signal 84 producing the dispensing gap between two opposing diaphragms which is needed for the apparatus 200 thereby enabling the electrostatic muscle to operate as a valve.

Figure 6F:
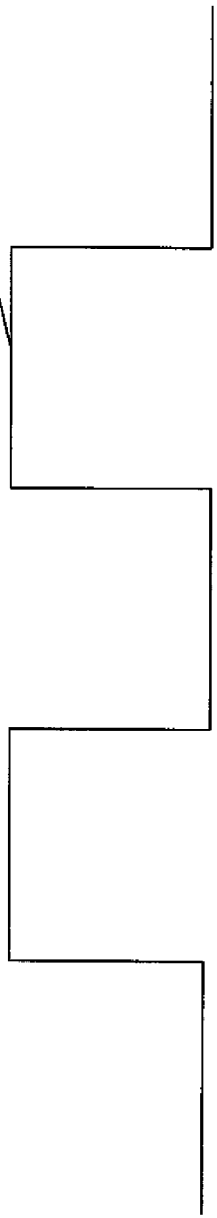
FIG. 6f is a graph of flow as a function of time showing valve-pump performance.

FIGS. 6, 6a, 6b, 6c, 6d and 6e are a description of the valve actuating mechanism. In one embodiment, the apparatus uses "electrostatic muscles", with an electric field 124, which induces strain on the natural axis 126, thereby yielding a strain proportional to the field 124 which acts as a valve actuating mechanism capable of dispensing the agents located in the synthetic skin pouch 200. The activity of the pouch 200 and the dispensation rate, described further in connection with FIG. 6f as 119, is controlled by the electronic scheme as noted in FIG. 2, using the bimorph piezoelectric layer. The cantilever beam action or strain is than plotted on the vertical axis shown in FIG. 6a in a characteristic hysteresis curve 122 and electrical field strength 124 is shown on the horizontal axis. The direction of strain of the cantilever beam acting as the valve gate dependent on the bonding material, the elastic plate's dimensions, and the electric field applied across the thickness of the material. Strain is produced on the piezoelectric element transversely as shear and radially as compression or tension as shown in FIG. 6b as a result of the applied field 124. The applied field on the X axis 91 produces strain as a result of the radial tension along the X-axis and is shown as 94, similarly the applied field on the Y-axis 92 produces strain as a result of the radial tension along the Y-axis and is shown as 95, and the applied field on the Z-axis 93 produces strain as a result of the radial tension along the Z-axis and is shown as 96. The radial strain causes the surface of the passive plate to expand and contract which causes the entire element structure to bend.

One embodiment of the actuating mechanism is shown in FIG. 5c, where two piezoelectric diaphragms 80 are mounted in opposition to each other. The displacement or mechanical distortion due to the piezoelectric effect produces a gap, acting as a flow channel. The piezoelectric actuator is a bimorph made by bonding two pieces of piezo-ceramic such as, for example, barium-titanate and lead-zirconate-titanate formed together so as to produce the differential change in the length of the two plates. This element has two transverse expender plates secured together face to face in such a manner that a voltage applied to the electrodes causes the plate to deform in opposite directions, resulting in a bending action. The displacement of the bimorph in response to voltage applied is of the order of 10 μm per volt. The bimorph lever provides the motion which induces the displacement and hence opens the valve of the pouch where the medicating agents or chemotherapeutic and/or biological response modifiers are stored thereby inducing the transfer of the agents to the surface of the biological tissue (i.e. Tumor).

The valve actuating motion due to the non-centrosymmetric characteristics of the piezocrystal coupled with the bimorph geometry created under applied voltage (poled ceramic) changes the dipole moment, thereby creating a nearly linear displacement due to the shear strain that occurs. As previously noted this operation is further explained in FIG. 5c.

The basic description of the valve actuating mechanism shown in FIG. 6 serves as a general guideline for the behavior of the microcontroller, 401. When a polarization P, is induced in the piezoelectric bimorph by an applied electric field E, the crystal suffers a small strain S, which is proportional to the polarization P. This electrostrictive strain generates the displacement. A matrix formulation of this relationship, where the six components $T_j$ of the stress tensor (three compressional components and three shear components) to the three components $P_i$ of the polarization vector described by a matrix of 18 piezoelectric moduli $D_{ij}$.

The same scheme ($D_{ij}$) also relates to three components $E_i$ of the electric field to the six components $S_j$ of the strain.

The direct effect is obtained by reading this scheme in rows as in equation (1) shown below:

$$P_i = -\sum_{j=1}^{6} d_{ij}T_j \quad i = 1, 2, 3$$

and by reading it in columns as in equation (2) as shown below:

$$S_j = \sum_{i=1}^{3} d_{ij}E_i \quad j = 1, 2, \ldots 6$$

|  |  | Compression: | | | Shear: | | |
| --- | --- | --- | --- | --- | --- | --- | --- |
|  |  | $S_1$ | $S_2$ | $S_3$ | $S_4$ | $S_5$ | $S_6$ |
| $E_1$ | $P_1$ | $d_{11}$ | $d_{12}$ | $d_{13}$ | $d_{14}$ | $d_{15}$ | $d_{16}$ |
| $E_2$ | $P_2$ | $d_{21}$ | $d_{22}$ | $d_{23}$ | $d_{24}$ | $d_{25}$ | $d_{26}$ |
| $E_3$ | $P_3$ | $d_{31}$ | $d_{32}$ | $d_{33}$ | $d_{34}$ | $d_{35}$ | $d_{36}$ |

An analogous matrix $e_{ij}$ relates the strain to the polarization and the electric field to the stress as in equations (3) and (4) shown below:

$$P_i = \sum_{j=1}^{6} e_{ij}S_j \quad i = 1, 2, 3$$

$$T_j = \sum_{i=1}^{3} e_{ij}E_j \quad j = 1, 2 \ldots 6$$

The number of independent matrix elements $d_{ij}$ or $e_{ij}$ depends upon the symmetry elements of the crystal, but since the apparatus disclosed uses a specific higher symmetry, the resultant iteration will be limited to one independent element in the matrix ($d_{ij}$) and the symmetry matrix takes its simplest form when the natural symmetry axes of the piezoelectric crystal are chosen for the coordinate system, as shown in FIG. 6b. The matrix described above is the algorithm by which the microcontroller 401 identifies the duty cycle 119 shown in FIG. 6f. The polarization and the respective opening and closing value of the valve actuating mechanism are shown in 6c, and 6d. Furthermore FIGS. 6c and 6d show a graphical representation of the valve actuating mechanism where the two bimorph piezoelectric elements forming the valve gate are shown in operation. In FIG. 6c the piezoelectric element is shown in its "extended state" 118 and in FIG. 6d the piezoelectric element is shown in its "compressed state" 117. The pouch 200 is compartmentalized into three compartments a, b, and c of medicating pouch 200, and is opened as a result of the excitation of the polarizing field as shown in FIG. 6c. The remaining compartments are in a "closed state" as shown in FIG. 6d. Hence dispensing of the medicating agent of the specific kind for the duration defined by the microcontroller 401 can take place from compartment "a" but not from the other compartments. This action is repeated in accordance with the protocol defined by microcontroller 401 and its lookup tables residing in memories 445, 446, and 447, as shown in FIG. 2.

Figure 6E:
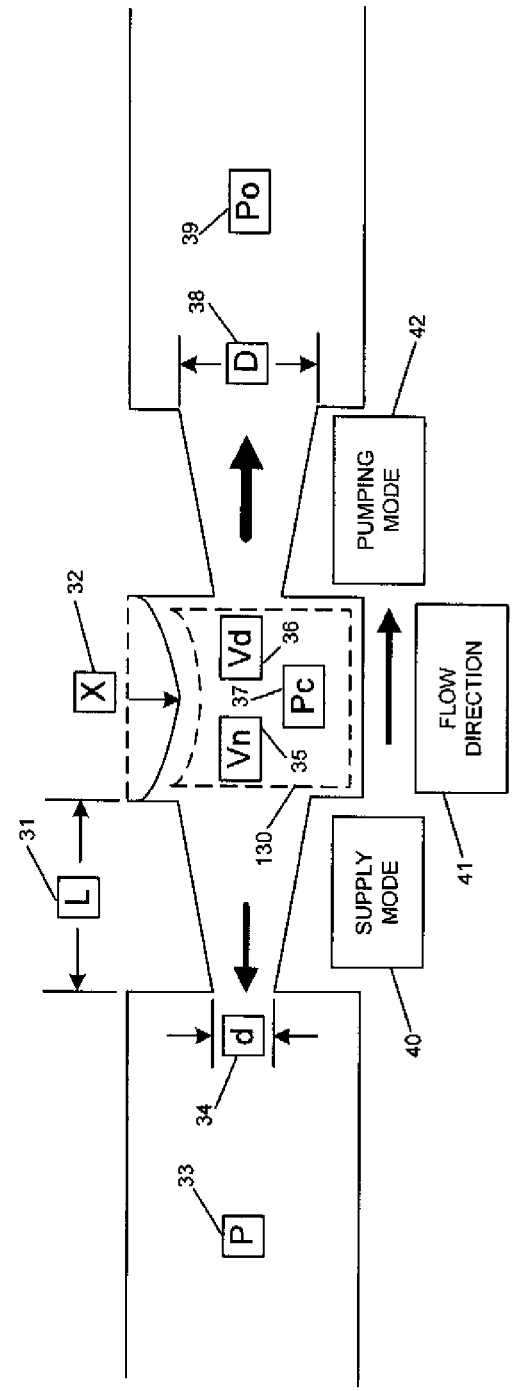
FIG. 6e is a diagrammatic representation of the respective duty cycle signal applied in the supply and pump modes.
Figure 6G:
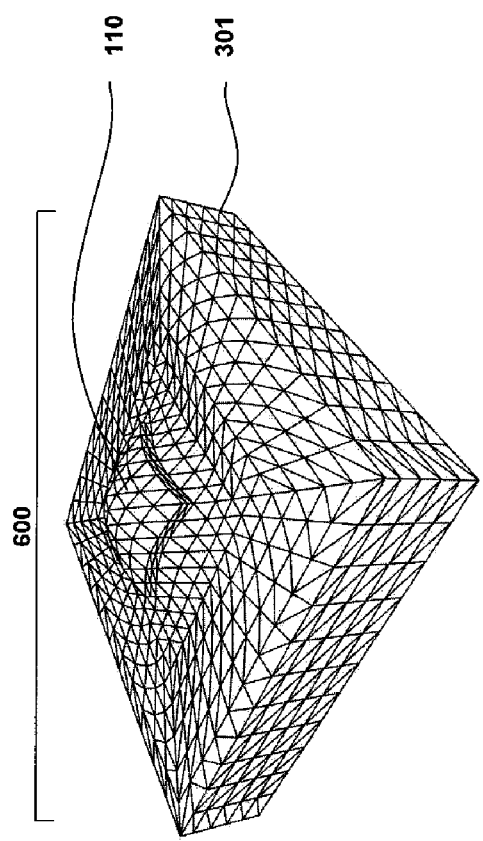
FIGS. 6g and 6h are finite-element graphical representations of the deformation of the "electrostatic muscle".
Figure 6H:
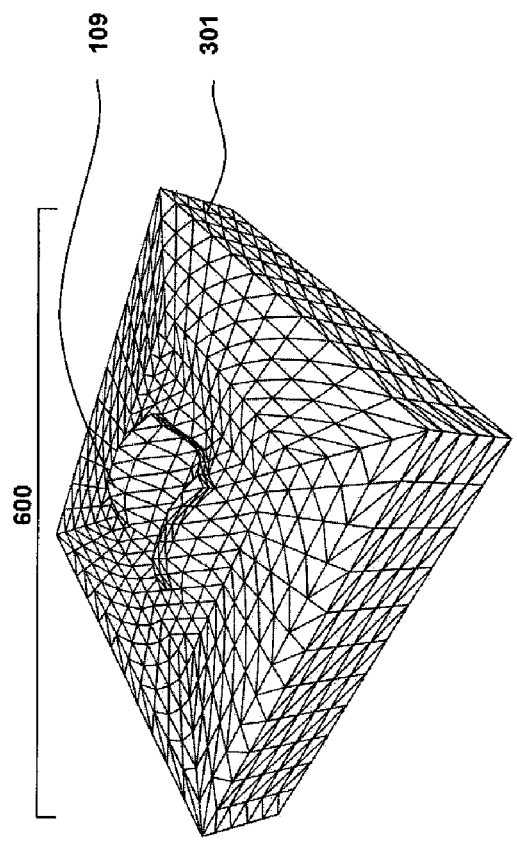

FIG. 6a illustrates how polarization of the "electrostatic muscle" 600 depicted in FIGS. 6g and 6h produces shear strain. The figure shows the hysteresis associated with the behavior of the piezoelectric device. At the starting point, which is the origin of the curve, the curve shows the intersection of the horizontal axis, the field axis, 124, with the vertical axis, the polarization axis, 125. The piezoelectric device has no field or polarization applied at this point. When field is applied across the device, it starts to exhibit some polarization, shown as a virgin curve, 122, which reaches some maximum and plateaus out. Upon the removal of the field from the device, the polarization exhibits some hysteresis, and the return path, 121, is different from the original path that the curve took. Due to the hysteresis present in the device the process repeats itself through a new path, 123, and returns again through the original curve 121.

FIG. 6b shows the 3-Dimensional three dimensional space in which the polarization of the "electrostatic muscle" 600 takes place. No translation is associated with the device, and the bending produces partial rotations in the three axes as shown, the X axis, 91, the Y axis, 92, and the Z axis, 93. The corresponding rotational bending produced along these axes is 94, 95 and 96, corresponding to the three axes X, Y, and Z, respectively.

FIGS. 6c and 6d depict the piezoelectric valve assembly, 301, in operation. FIG. 6c shows the "electrostatic muscle" 600 in its open state, 117, which is also the pump mode, 110, and FIG. 6d depicts the "electrostatic muscle" 600 in its closed state, 118, which is also the supply mode 109, where the medicating agents or BRMs are pumped out and transported from the pouch chambers 201, 202, 203, to the desired tumor site or biological tissue of interest. In FIG. 6d the inlet nozzle is shown as 108, while an increasing chamber volume 101 is taking place. This increase in chamber volume causes flow 105 from the inlet to enter the chamber 130 and at the same time there is a small amount of fluid 106, which flows from the outlet 107 into the chamber 130 as well. However because of the venturi action of the inlet 108 and the outlet 107, the total net flow is from the medicating pouch chambers 201, 202, and 203, into the chamber 130. In this case the inlet 108 exhibits a diffuser action, 104, and the outlet 107 exhibits a nozzle action, 103. FIG. 6c shows the "electrostatic muscle" 600 in its open state, 117, which is also the pump mode, 110. In this case there is a decrease in chamber volume 102, which causes a net flow to take place from the chamber 130 to the tumor site through the outlet 107. Although there is a small amount of flow 106 from the chamber 130 to the inlet, the net flow 105 is substantial and is from the chamber 130 to the tumor site. In this mode the inlet 108 exhibits a nozzle action 103 and the outlet exhibits a diffuser action, 104.

FIG. 6e shows the mathematical entities associated with the piezoelectric valve assembly 301. For the sake of clarity the figure shows the valve in its open mode, similar to the mode of operation shown earlier in FIG. 6c. The chamber 130 is shown with decreasing volume, hence increasing the chamber pressure, where the total pressure inside the chamber is shown as $P_c$, 37. The pressure at the inlet is shown as $P$, 33, impinging onto the inlet, which has the diameter of d, 34. The inlet is shown in its supply mode, 40, and a net flow of fluid is transported from the inlet to the chamber, 130, through the inlet nozzle shown previously in FIG. 6d as 108, and which has a length L, 31. Upon entering the chamber 130 the fluid has a reduced velocity due to the Venturi action of the inlet nozzle 108, where the velocity is denoted by $V_n$, 35. The fluid exits the chamber 130 at the right and enters the outlet nozzle which was previously shown in FIG. 6*d* as 107, with an exit velocity of $V_d$, 36. The outlet orifice, 107, which is in the pumping mode, 42, has an exit diameter D, 38, and creates an output pressure P.sub.0, 39, in the outlet nozzle 107. The net direction of the flow is shown as 41. The displaced volume of the chamber 130 is shown as distance X, 32, where this action is further clarified in FIGS. 5*a* and 5*b*. As noted in FIGS. 5*a* and 5*b*, the rate of flow of the medicating agent from the pouch 200 is governed by the rate of decrease in chamber volume of the electrostatic muscle 600, through the use of the microcontroller 401.

FIG. 6*f* is a representation of the respective duty cycle of the applied voltage signal, 119, showing the change in its polarity which causes the piezoelectric device to change states.

FIGS. 6*g* and 6*h* are a finite-element graphical representation of the "electrostatic muscle" 600, depicting the valve actuating mechanism, 301, 302, and 303, where in FIG. 6*g* the valve 301 is shown in the supply mode and where the piezoelectric diaphragm is displaced as to achieve an increase in the chamber volume 101, thereby providing the action to form the geometry which supports the supply mode, 109, of the "electrostatic muscle" 600. FIG. 6*h* further expresses the behavior of the "electrostatic muscle" 600 in the pump mode 110, where the diaphragm shown in 301 is displaced in such a way as to decrease the chamber volume 102 and to pump out the medicating agent previously described. The method of operation of the bimorph action which is described in detail in FIGS. 5*a* and 5*b*, is to use the piezoelectric effect in order to excite the diaphragm at its natural frequency, hence resulting in a large scale motion which pumps the medicating agent from the pouch 200 chambers, depicted in FIG. 6*i* as medicating agents 201, 202, and 203, respectively. The two end states of the diaphragm, 109 and 110, are shown where the maximum stresses occur near the edge of the assembly, 301.

Figure 6I:
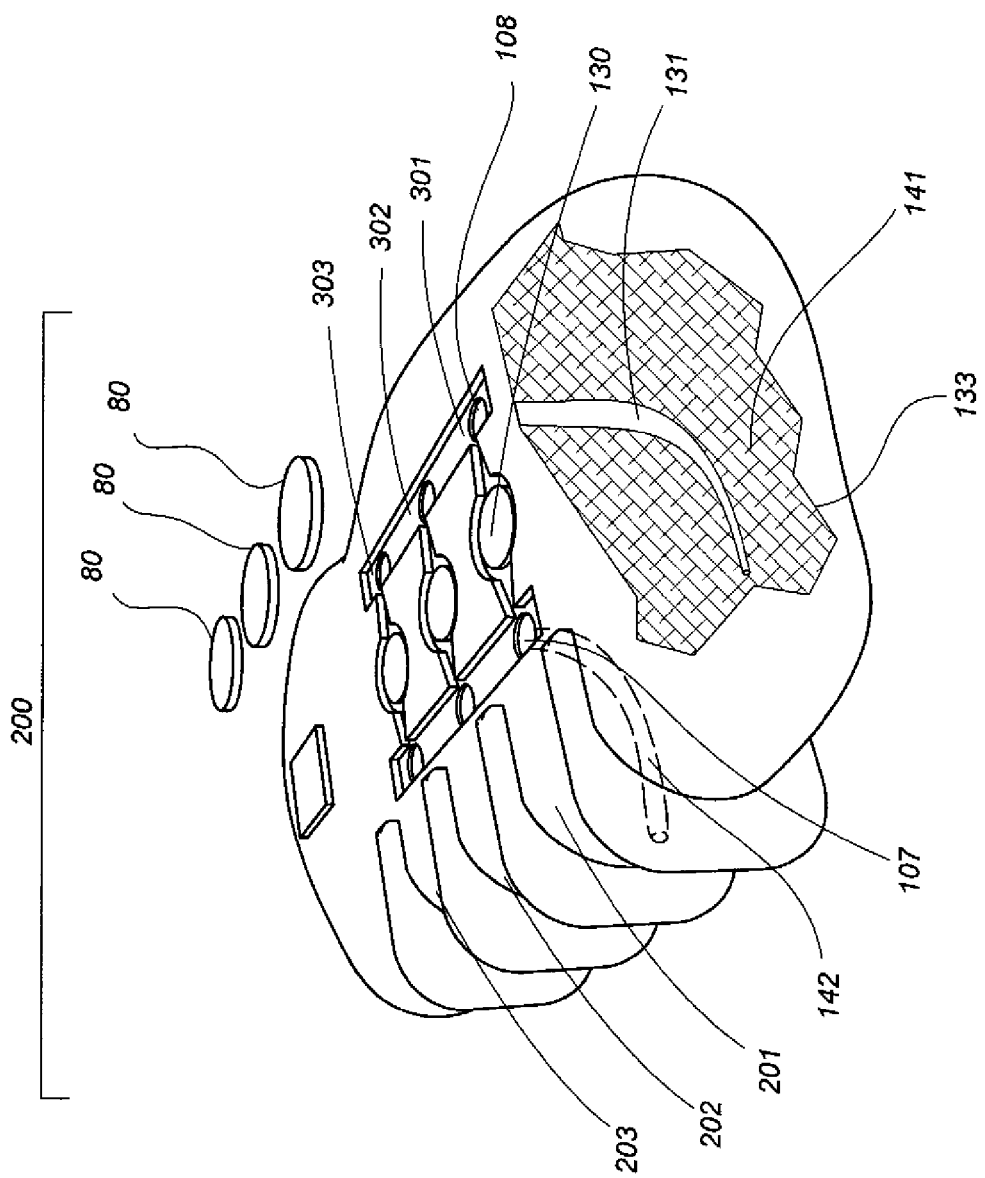
FIG. 6i is a perspective view of the valve-pump in partially exploded view.

FIG. 6*i* is a three dimensional pictorial representation of the apparatus, showing the pouch 200 with the three individual sections of the "electrostatic muscle" 301, 302, and 303, associated with the three compartments of the medicating agents 201, 202, and 203, respectively. The piezoelectric valves are shown on the top portion of the figure in exploded view as item 80, with their associated chambers 130. For clarity one section of the "electrostatic muscle" is also shown with its inlet, 108, and its outlet, 107. A cutaway section 133 of chamber for medicating agent 201 is shown, with the inlet tube 131 leading to the inlet 108 of "electrostatic muscle" 301. As previously shown in FIG. 2, during operation microcontroller 401 commands the driver circuits 405, 406, and 407, through their respective AND gates 416, 417, and 418, to turn on transistors 466, 467, and 468, respectively, thereby creating an oscillating voltage across the piezoelectric elements, 471, 472, and 473, respectively. When said piezoelectric elements 80 are activated, a flow of medicating agent 201 is pumped from the corresponding pouch through the inlet tube 131 through the inlet 108 and into the valve chamber 130. The piezoelectric elements then change state upon a command from microcontroller 401 thereby moving the medicating agent 201 from the valve compartment 130 and to outlet tube 142 typically shown for chambers for medicating agent 201, and repeated for the chambers for medicating agents 202, and 203, and onto the desired tumor site. As noted previously, a more comprehensive description of the valve/pump mechanism is shown in FIGS. 6*c* and 6*d*.

Figure 6M:
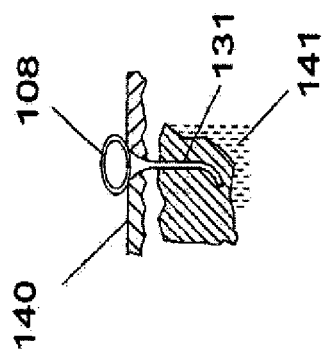
FIGS. 6j, 6k, and 6m, are perspective views of the scaffolding of the pouch.
Figure 6K:
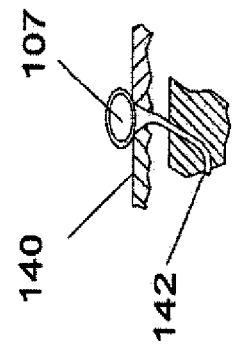
Figure 6J:
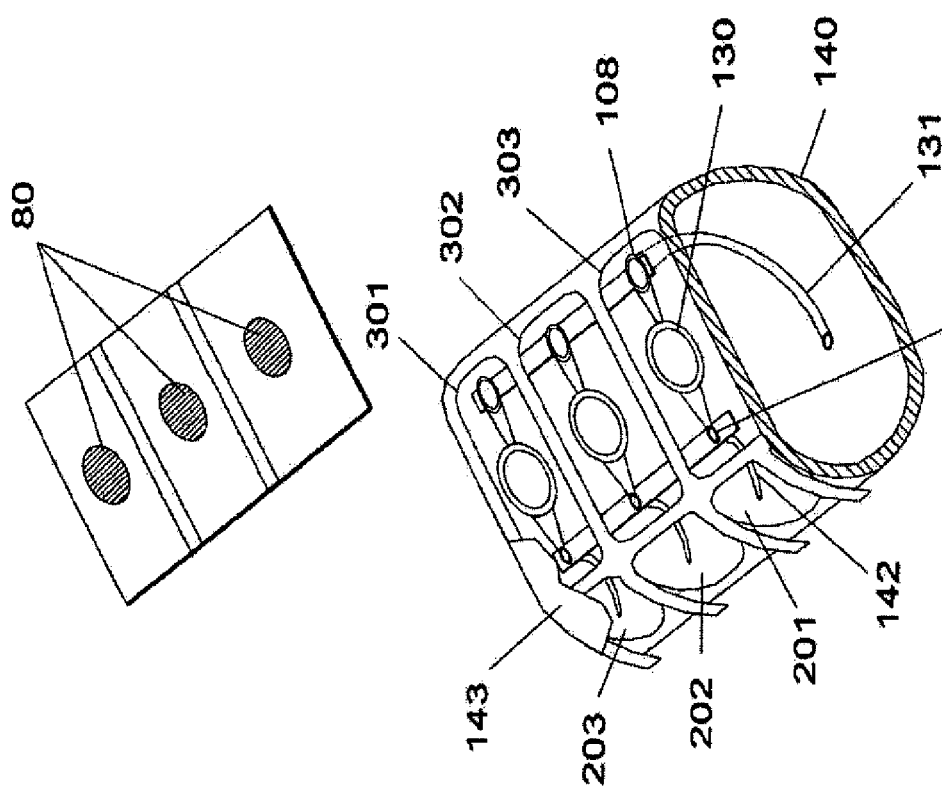

FIGS. 6*j*, 6*k*, and 6*m* are an depictions of the scaffolding 140 comprised of a matrix formed out of collagen material, such as the substance made by Collagen Matrix, Inc. and formed with the geometry supporting the structure noted in FIG. 6*i*, with the three compartments, comprising of the chambers containing the medicating agents 201, 202, and 203. FIG. 6*j* shows the pumps 301, 302 and 303, with their main components, the inlet tubes 131 and the pump inlet 108, where 108 is further detailed in FIG. 6*m*. The chambers, 130, and the outlet 107 with its outlet tube 142, is further detailed in FIG. 6*k*. FIG. 6*j* further depicts the piezoelectric valves, 80, shown in exploded view for clarity with respect to the main body of the pump mechanism, where each of piezoelectric elements 80 corresponds to its appropriate chamber 130. A small portion of the outer layer of the synthetic skin 143 is partially shown as a cover where in actuality the synthetic skin layer such as the one made by Integra Life Sciences and commonly known on the market as Integra, or FortaPerm, also shown in FIG. 6*j* as item 143, made by Organogenesis Inc. covers the pouch as pictorially depicted by FIG. 6*i*. Both materials are biodegradable by design and timed for gradual disintegration inside the human body. The use of skeletal structure 140 for the pouch 200 is formed out of substance such as Collagen, has the benefits of structural stability dependant on the matrix thickness and its geometry. In addition the collapse of the chambers coincides with the depletion of the medicating agents 201, 202, and 203, inside the chambers. The material provide biomechanical strength and support; it exhibits resistance to cellular infiltration, remodeling and degradation. The skeleton 140 is biocompatible with human tissue and has no antigenicity. The collagen matrix is consistent in its behavior and predictable in performance, and it can be formed to meet the geometry of the pouch 200.

Figure 7:
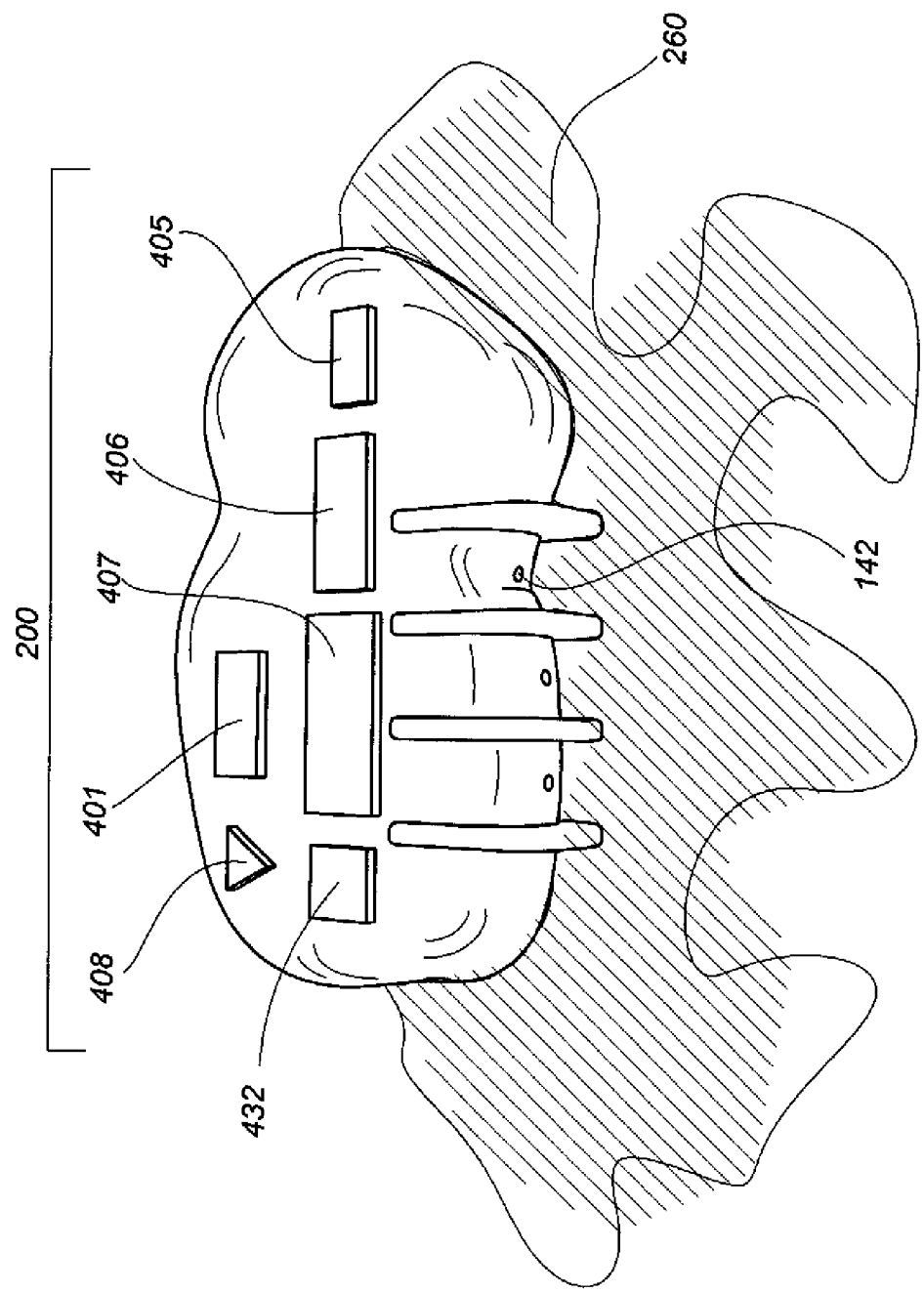
FIG. 7 is a perspective view of the apparatus partially engulfed by a tumor structure.

FIG. 7 shows the apparatus 200 partially engulfed by a tumor structure. One example is the use the apparatus 200 in DCIS, ductal carcinoma in situ, 260, which is the most common type of noninvasive breast cancer in women. The figure further depicts a relationship between the medicating pouches and the electronic scheme. After performing a small incision in the outer layer of the skin and possibly the soft tissue of the body, a physician will lay a pouch 200 with its associated electronics 100 and embedded sensor bank 300 over a solid tumor, as for example 260. The pouch contains the appropriate medicating agent(s) to be dispensed locally, and upon command by the preprogrammed routines residing in the look-up tables the apparatus initiates a controlled delivery of the medicating agents. The medicating agent which is dispensed automatically by the apparatus with its preprogrammed routines can have its parameters modified with the use of the external control modality 500 shown in FIG. 9. An active control and regulation of the administration of medicating agents is thus achieved through the attached control mechanism 100 to the synthetic pouch 200 and with the aid of a piezoelectric valve actuating mechanisms 463, 464, and 465. The apparatus is thus capable of administering the proper dose and timing of delivery and duration, which is controlled by the microcontroller 401, and reporting of the events in the tumor site through the use of RF transmitter 451, without the traditional side effects known to those familiar with the art. The biomodulation action disclosed by the system is described as manipulating the metabolic pathway of a cytotoxic drug to increase the efficacy of selective protection of normal tissue. The target of modulations includes specific enzymes of drug metabolism, receptors for adhesion or growth, cell cycle phases, gene expression and immune system, which are reported to the clinician via the RF link using transmitter 451. The expressions of the medicating agents (BRMs or chemotherapeutic) can be further modified by the clinician using the RF receiver link 449, in conjunction with the external controller 500. Proper dosing and scheduling to obtain maximum benefits is the centerpiece of the system when considering a combination of chemotherapy with biotherapy. The emergence of combination therapy such as IFN-.alpha. with 5-FU (5-fluorouracil) and chemotherapy paired with IL-2 and IFN-.alpha. is further explored in the application of the system and potential use of such an apparatus in improving the effectiveness of tumor elimination by the use of the system. Toxins can be used to induce an immune response which activated the immune system to eliminate or reduce the tumor burden. It is useful to use an administration cycle of BRMs and chemotherapeutic agents on a scale and measure which does not lend itself to the traditional approach of maximum tolerated dose. Hence, the ability to regulate and schedule the dose of the BRMs and/or chemotherapy is essential and is addressed by this system. A novel approach to tumor treatment is disclosed, outlining the benefits of local and improved combination therapy for solid tumor. The approach incorporates the findings and observations from clinical studies and demonstrates how the disclosed apparatus and method 200 yields a better correlation between BRMs using cytokines such as Interferon (IFN), Interleukins (IL), Hematopoietic factors (HGF), Monoclonal antibodies (MAB), and Tumor Necrosis Factor (TNF) in combination therapy with chemotherapeutic agents in achieving the desired goal of a complete response. Since BRMs cascade effects are somewhat known to those familiar with the art, and chemotherapeutic effects of cell death is a preprogrammed event, the use of the apparatus 200 with its associated circuitry will enhance and/or modulate a variety of tumor growth factors and will enable a combination therapy to take place at the tumor site without the known side effects due to maximum dose of toxins. The ability of the apparatus 200 to change its preprogrammed sequence of events, such as release of various agents on a specific schedule and dose due to the innate capability of the apparatus 200 to receive commands via communication links through the use of the RE receiver 449 and the RF transmitter 451, offers a treatment change in mid-stream by transmitting program codes, which instruct the microcontroller 401 to enhance one process or another. The chemoimmunotherapy model, by the use of the disclosed apparatus 200, will enable the clinician to perform a selective treatment, by preprogramming the targeted results. A typical example cited by clinical observation is [Interferon alpha. and 5 fluorouracil and calcium liucovorin] and combination of [dacarbazine, BCNU, cisplatin, and tonoxifen followed by interferon .alpha. and IL-2]. The system disclosed in FIG. 9 enables the clinician to administer BRMs and chemotherapeutic agents on schedule as well as duration and sequence preprogrammed to meet clinical observations with the intended goal of meeting complete response.

There are a number of parameters which can be used to determine the dosage of a medicating agent given to a particular patient, such as age, sex, weight, current medical condition and more. The apparatus is capable of monitoring the distribution of the medicating agent over time which allows the clinician to tailor the dosage to the specific needs of a patient. Moreover, the patient's illness history varies from hour to hour and from day to day. Prescribing the drug for a period of a week or a month in advance without the ability to monitor essential markers and other similar agents in the blood creates a situation where the biological resistance to the drug is elevated, and an increased dosage of the medicating agent will cause less than improved result. Hence the controller 401 utilizing fuzzy logic algorithm residing in memories 445, 446 and 447 as part of its control loop will alleviate the over-dependence of the patient on Gaussian distribution of the drug, as over-medication will be avoided and side effects such as toxicity can be reduced.

FIG. 8 shows three possible cases of the application of the pouch 200 as it is placed inside the body. The figure illustrates the apparatus implanted in tumor sites: 8*a*, Ductal Carcinoma of the breast (DCIS), 8*b*, Meningioma in the pertiorcular region of the head, and 8*c*, Transverse Colon tumor. A detailed description of the implementation of the apparatus 200 is further illustrated in FIG. 7.

Figure 9A:
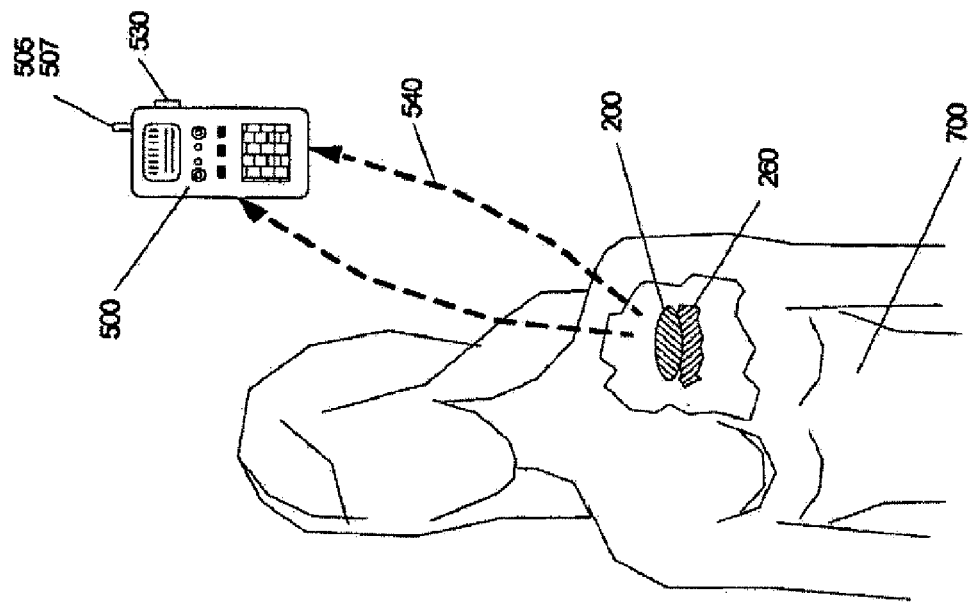
FIG. 9a is a graphic diagram of the implantable pouch and its associated communications controller.
Figure 9:
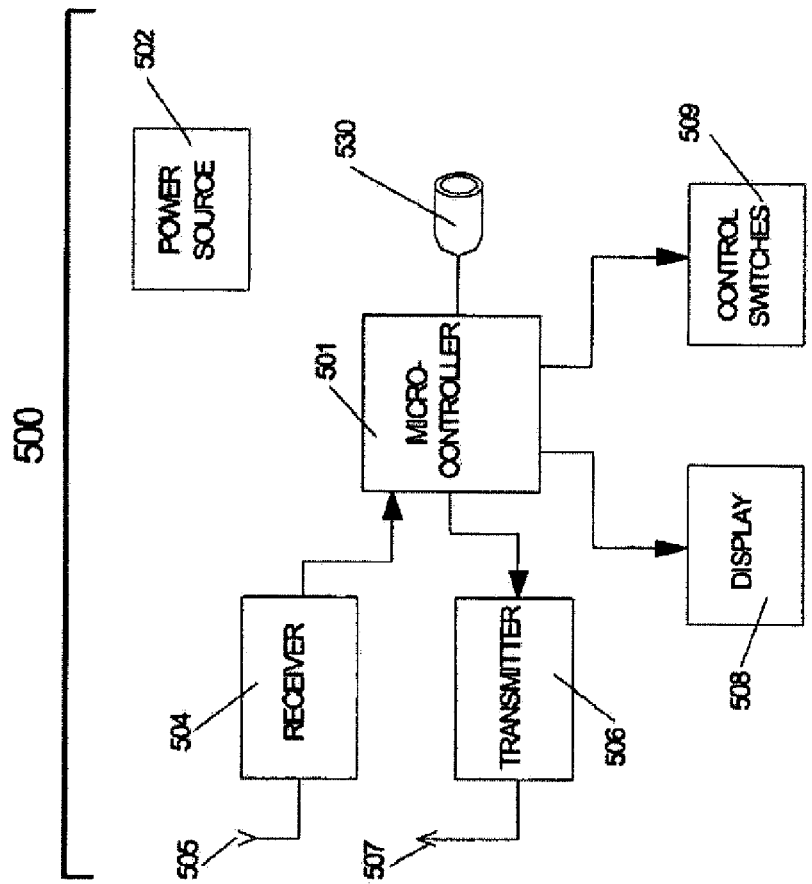
FIG. 9 is a high level block diagram of the external control unit which communicates with the implanted apparatus.

FIG. 9 shows an external data 500 logger which communicates with the internal pouch, 200. The medicating pouch 200 communicates with the external controller 500 by the use of its RF Transmitter 451 and its associated antenna 460 and RF Receiver 449 and its associated antenna 461. After implantation of the pouch in the tumor 260 inside the patient 700 the system allows for programmability of the device in order to dispense the medicating agent 141 in proper intervals over time and in the prescribed doses. Once the apparatus 200 is implanted and is in operation, the clinician may decide to change the parameters of the operation such as the amount of the medication dispensed onto the tumor site 260 or the time intervals associated with the dispense process. The clinician communicates with the internal electronics of the pouch 200 using an external programming device 500, shown in the figure, which may be in the form of a desk-top computer or any other similar appropriate device. The device 500 is able to communicate with the microcontroller 401 through its own microcontroller 501 via RF transmitter 506, its antenna 507, and the RF receiver 504 and its antenna 505, or via the serial communication port 530, located in the external control box 500. The new sets of commands are then transferred to the medicating pouch 200. These new command data are then stored in the memory of the microcontroller 401, and the apparatus is now programmed anew to perform the procedure as coded in the new instruction set.

Microcontroller 401 located in the pouch 200 and implanted inside the patient's body 700 communicates with the external controller 500 via RF transmitter 451 and RF receiver 449 thereby sending its collected data to the external data logger 500. This feature enables the clinician to collect data and to determine the state of the patient throughout the period of treatment. These data are stored inside the external controller providing chart history of the treatment and the status of the parameters associated with the tumor site for example 260. The pouch 200 transmits data for collection and storage. The data logger shown in 500 is controlled by the user via its set of control switches 509, and it also displays the amount of medicating agent dispensed over time by the pouch 200 on its display, 508. Data collected in this manner can be used to correlate behavior pattern of a particular patient and his or her chart history. One can write a data collection and analysis program which can be displayed by controller 500. Once the data are collected from the microcontroller 401 located in pouch 200, the external controller 500 or the host PC can then plot the data on a time scale and analyze the data further. It is significantly better to correlate between the input and the output, or between cause and effect as to mirror the action of the pouch 200 and its host tumor site 260. Such data in the form of historical plot of cause and effect benefit the patient and aide in future research. The entire unit as shown in the figure is run by power obtained from its power source, 502.

FIG. 9*a* is an illustration of a female patient 700 with tumor of the form ductal carcinoma (DCIS) 260 with the implanted pouch 200. The controller 500 with its associated serial port 530 and receiver and transmitter antennae 505 and 507 respectively is shown in its bidirectional communication mode with the implanted pouch 200 via the RF path 540.

Although specific features of this system are shown in some drawings and not others, this is for convenience as each feature may be combined with any or all of the other features in accordance with the system.

Other embodiments will occur to those skilled in the art and are within the following claim.

Although the preceding descriptions contain much specificity, this should not be construed as limiting the scope of the system, but as merely providing illustration of the preferred embodiment thereof.

It is understood that the above description is intended as an illustration and various embodiment of this system have been described herein. The description of the apparatus and method of this system is not intended to be limiting on this system, but is merely illustrative of some embodiment of this system. Other apparatus and methods which incorporate modifications and changes to that which have been described herein, are equally included within this application. Additional objects, features and advantages of the present system will become apparent by referring to the above description of the system in connection with the accompanying drawings. Thus, scope of the system is limited only by the claims.

What is claimed is:

1. An implantable apparatus for infusing a plurality of medicating agents to a specific desired location at a tumor site for nonsystemic treatment of a tumor, when implanted within a patient's body, comprising:
    an implantable pouch having a plurality of collapsible and disintegratable chambers composed of a bioabsorbable material, the pouch comprising a scaffolding forming a matrix capable of degrading over time, and a synthetic human skin for substantially enclosing the pouch, the chambers being structurally defined by the matrix, each chamber having a volume for storing a corresponding one of the plurality of the medicating agents in a macroscopic amount and for a duration effective for tumor treatment including relatively long durations, and wherein the chambers and the synthetic human skin are arranged and configured to substantially completely collapse and disintegrate within the patient's body with depletion of the plurality of medicating agents which is selectively dispensed from the chambers;
    where the plurality of medicating agents are stored in corresponding ones of the plurality of collapsible chambers;
    multiple implantable piezoelectric pumps fabricated in the pouch which pumps form a skeleton for the pouch, the pumps being configured to transfer the medicating agents to the patient;
    where the synthetic human skin is an implantable and bioabsorbable skin substitute;
    at least one implanted sensor to measure a local homeostatic response related to at least one of the plurality of medicating agents; and
    an implanted control circuit with a programmable memory on a biodegradable substrate housed within and implanted at the site of implantation of the pouch and proximate to the pumps to control optimal local dosing amounts of each of the medicating agents and scheduling of the medicating agents in a closed loop control mode so that control of the operation is performed autonomously as determined by adjustable values of locally sensed homeostatic parameters at the treatment site,
    where the control circuit controls at least one of the piezoelectric pumps to modify the state of the tumor in response to measurements from the implanted sensor, and where the control circuit controls and selectively adjusts the scheduling of the amounts of the medicating agents which are delivered in response to selective user commands delivered to the control circuit and alterable during a treatment process after implantation.

2. The apparatus of claim 1 where the control circuit to control the piezoelectric pumps provides for autonomously regulating, controlling, and modulating a combination therapy of cytokine and chemotherapeutic agents for the purpose of tumor elimination in a closed loop control mode.

3. The apparatus of claim 1 where the control circuit to control the piezoelectric pumps autonomously administers less than the maximum tolerated dose of at least one medicating agent in the closed loop control mode.

4. The apparatus of claim 1, said at least one medicating agent comprising at least one of, a cytotoxic agent, a pleiotrophic agent, and an agent having both cytotoxic and pleiotrophic properties.

5. The apparatus of claim 1 further comprising control logic to control said at least one piezoelectric valve, said control logic configured to change a sequence of events, such as release of various agents on a specific schedule and dose due to the innate capability of the apparatus to receive commands via communication links, thereby offering a treatment change in mid-stream by transmitting program codes, which instruct the microcontroller to enhance one process or another.

6. The apparatus of claim 1 further comprising control logic to control said at least one piezoelectric valve to regulate and schedule a dose of said medicating agents.

7. The apparatus of claim 1 further comprising control logic to control said at least one piezoelectric valve to provide combination therapy for solid tumor.

8. The apparatus of claim 1 further comprising control logic to control said at least one piezoelectric valve to provide selective treatment comprising at least one of:
    Interferon $\alpha$ and 5 fluorouracil and calcium liucovorin combination of dacarbazine, BCNU, cisplatin, and tonoxifen followed by interferon $\alpha$ and IL-2.

9. The apparatus of claim 1 further comprising control logic to control said at least one piezoelectric valve to control release of said medicating agents based on tumor-specific behavior.

10. The apparatus of claim 1 further comprising sensors to monitor at least one of a temperature, a pH level, and a pressure in a tumor region.

11. The apparatus of claim 1 further comprising sensors and control logic to monitor biometric measures and indications of the behavior of a tumor and a treatment history.

12. The apparatus of claim 1 further comprising a sensor to measure pH.

13. The apparatus of claim 1 further comprising pressure and temperature sensors.

14. The apparatus of claim 1 further comprising a processor and software module configured to differentiate malignant versus normal cells due to lack of specificity of the cancer cell.

15. The apparatus of claim 1 further configured to measure pressure between a tumor site and the pouch.

16. The apparatus of claim 1 further comprising logic to administer said medicating agents on schedule as well as duration and sequence.

17. The apparatus of claim 1 configured to deliver said medicating agents by the use of electronic control of said piezoelectric pump.

18. The apparatus of claim 1 further configured to provide infusion of biological response modifiers in combination with chemotherapeutic agents.

19. The apparatus of claim 1 wherein each said piezoelectric pumps comprise a piezoelectric layer-wise pumps and valve.

20. The apparatus of claim 1 further comprising an electronic control module to control said piezoelectric pumps to provide timed release of said medicating agents.

21. The apparatus of claim 1 further comprising a software module to control said piezoelectric pumps.

22. The apparatus of claim 1 further comprising a software module to control said piezoelectric pumps to provide for controlled-delivery of the multiple medicating agents.

23. The apparatus of claim 1 further supports controlled delivery of chemotherapeutic agents and BRMs which is achieved by the use of an electronic timer and a microcontroller.

24. The apparatus of claim 1 further comprising a software module to control said piezoelectric pumps to provide an apparatus having multiple chambers, providing the clinician the ability to deliver a set of multiple medicating agents to the tumor site.

25. The apparatus of claim 1 further comprising a software module to control said piezoelectric pumps to provide an irrigation action which allows for the bioavailability of said medicating agents.

26. The apparatus of claim 1 further comprising a software module to control said piezoelectric pumps to provide an irrigation action for delivery of said medicating agents to provide improved penetration and treatment of tumors.

27. The apparatus of claim 1 further comprising a software module to control said piezoelectric pumps to provide an irrigation action for delivery of said medicating agents to refractory nature of a tumor by enhancing angiogenetic action at the tumor site.

28. The apparatus of claim 1 further comprising a software module to control said piezoelectric pumps to provide an active pumps and valve to provide control of dosage and timing of the medicating agents.

29. The apparatus of claim 1 further comprising a communications link.

30. The apparatus of claim 1 further comprising an implantable wireless bi-directional communications link coupled to the implanted sensor through the implanted control circuit and for communication of local homeostatic sensed bio-parameters to an external user.

31. The apparatus of claim 1 further comprising a digital communications link.

32. The apparatus of claim 1 further comprising an RF communications link.

33. The apparatus of claim 1 further comprising a communications link to provide control instructions to said piezoelectric pumps.

34. The apparatus of claim 1, where the piezoelectric pumps comprise a pressure generator to develop pressure along an axial path of an electrostatic valve.

35. The apparatus of claim 1 comprising the scaffolding to reduce clogging of the piezoelectric pumps with increased flow of the medicating agents.

36. The apparatus of claim 1 further comprising a pressure monitor.

37. The apparatus of claim 1 further comprising a control module to provide a voltage control of said piezoelectric pumps.

38. The apparatus of claim 1, where said piezoelectric pumps comprise a bimorph geometry.

39. The apparatus of claim 1 further supports a system where a continuous monitoring and reporting of biological response parameters are maintained in the resident memory of the system.

40. The apparatus of claim 1 further comprising a control system to control delivery of said medicating agents on a case-specific basis using a pre-programmed dosing schedule.

41. The apparatus of claim 1 further comprising a control system to control delivery of said medicating agents based on look-up-tables.

42. The apparatus of claim 1 further comprising a control system to control delivery of said medicating agents in real time.

43. The apparatus of claim 1 wherein said each of said piezoelectric pumps comprise a valve, said apparatus further comprising control logic to regulate the dispensation of medicating agents by modifying the duty cycle of the valve.

44. The apparatus of claim 1 further comprising control logic to regulate deliver of said medicating agents based on a pleiotrophic nature of said medicating agents.

45. The apparatus of claim 1 further comprising control logic to schedule delivery of said medicating agents based on toxicity and to allow for measures of bioavailability, solubility, concentration, and circulation based on locality.

46. The apparatus of claim 1 wherein said medicating agents comprise biomodulators.

47. The apparatus of claim 1 comprising control logic to deliver said medicating agents based on individual difference of different tumors.

48. The apparatus of claim 1 further supports the ability of the apparatus to mitigate the known factors such as peak serum concentration.

49. The apparatus of claim 1 further configured to evaluate the effectiveness of the medicating agents used during animal and clinical studies by providing the details and feedback on the use, dose, cycle, circadian time effects and the entire pharmacokinetic, as well as pharmacodynamic behavior of the medicating agents.

50. The apparatus of claim 1 further configured to be implanted in the neighborhood of the tumor site for effective local delivery of the medicating agents.

51. The apparatus of claim 1 further configured to provide a local administration of BRMs and chemotherapeutic agents to enhance mechanisms that support overlapping effects in reducing tumor burden and elimination of tumors.

52. The apparatus of claim 1 comprising a plurality of medicating agents for combination therapy, using one or more biological response modifiers to modify the relationship between tumor and host, hence modifying the host's biological response to tumor cells and chemotherapeutic agents.

53. The apparatus of claim 1, further comprising control logic to deliver said medicating agents by modulating the pharmacokinetics of the medicating agents as key enzymes, attenuation of drug resistance mechanisms, and modifications in permeability of the vascular system which allow increased accumulation of chemotherapeutic drugs at the tumor site, causing reduction of tumor burden.

54. The apparatus of claim 1 further supports the use of such modality to improve anti-tumor response and to increase production of cytokines, thereby decreasing suppressor mechanisms.

55. The apparatus of claim 1 comprising control logic to supports modalities of a patient's tolerance to cytotoxic effects.

56. The apparatus of claim 1 further comprising a software module to control said piezoelectric pumps to provide an apparatus to provide a dose and timeline to produce tumor burden elimination or reduction.

* * * * *